United States Patent
Holtcamp

(10) Patent No.: US 6,841,504 B2
(45) Date of Patent: Jan. 11, 2005

(54) POLYMERIZATION CATALYST ACTIVATOR AND ITS USE IN A POLYMERIZATION PROCESS

(75) Inventor: Matthew W. Holtcamp, Huffman, TX (US)

(73) Assignee: Univation Technologies, LLC, Houston, TX (US)

(*) Notice: Subject to any disclaimer, the term of this patent is extended or adjusted under 35 U.S.C. 154(b) by 252 days.

(21) Appl. No.: 10/058,571

(22) Filed: Jan. 28, 2002

(65) Prior Publication Data

US 2003/0171211 A1 Sep. 11, 2003

(51) Int. Cl.$^7$ .............................................. B01J 31/00
(52) U.S. Cl. ....................... 502/150; 502/102; 502/103
(58) Field of Search ................................ 502/150, 103, 502/102

(56) References Cited

U.S. PATENT DOCUMENTS

| | | | | |
|---|---|---|---|---|
| 5,233,049 | A | * 8/1993 | Dinan et al. | 548/462 |
| 5,539,124 | A | * 7/1996 | Etherton et al. | 548/402 |
| 5,744,417 | A | * 4/1998 | Nagy et al. | 502/155 |
| 5,756,611 | A | * 5/1998 | Etherton et al. | 526/127 |
| 6,147,173 | A | 11/2000 | Holtcamp | 526/133 |
| 6,211,105 | B1 | 4/2001 | Holtcamp | 502/103 |
| 6,335,466 | B1 | * 1/2002 | Strauss et al. | 564/9 |
| 6,462,156 | B2 | 10/2002 | LaPointe | 526/165 |
| 6,486,277 | B1 | * 11/2002 | Erker et al. | 526/134 |
| 6,495,484 | B1 | * 12/2002 | Holtcamp | 502/152 |
| 6,610,803 | B1 | * 8/2003 | Wenzel | 526/142 |
| 6,632,770 | B2 | * 10/2003 | Holtcamp | 502/158 |
| 6,632,901 | B2 | * 10/2003 | McCullough | 526/165 |
| 6,703,338 | B2 | * 3/2004 | Holtcamp et al. | 502/123 |

FOREIGN PATENT DOCUMENTS

| | | |
|---|---|---|
| EP | 0 568 151 A | 11/1993 |
| JP | 11 080224 A | 3/1999 |
| WO | WO 99/42467 A | 8/1999 |
| WO | WO 01/23442 A1 | 4/2001 |
| WO | WO 01/62764 | 8/2001 |
| WO | WO 01/62764 A1 * | 8/2001 ............. C07F/5/02 |
| WO | WO 02/08303 A | 1/2002 |

OTHER PUBLICATIONS

R. E. LaPointe, G.R. Roof, K. A. Abboud, J. Klosin, J. Am. Chem. Soc. 2000, 122, 9560–9561.

G. Kehr, R. Fröhlich, B. Wibbeling, G. Erker, Chem. Eur. J. 2000, 6, No. 2, 258–266.

R.E. LaPointe, G.R. Roof, K.A. Abboud, J. Klosin, J.Am. Chem. Soc. 122, 9560–9561 (2000).

G. Kehr, R. Fröhlich, B. Wibbeling, G. Erker, Chem. Eur. J., 6, No. 2, 258–266 (2000).

* cited by examiner

Primary Examiner—Mark L. Bell
Assistant Examiner—Jennine M. Brown
(74) Attorney, Agent, or Firm—Kevin M. Faulkner

(57) ABSTRACT

Disclosed are polymerization catalyst activator compounds which include a Group 13 atom, preferably boron or aluminum, bonded to at least one heterocyclic groups. The heterocyclic group preferably contains one or more heteroatoms selected from Group 15 and/or 16, and may be unsubstituted or substituted. Preferably, the heterocyclic ligand is substituted with a halogen atom or a halogen containing group, where the halogen is preferably fluorine. Also disclosed are olefin(s) polymerization processes utilizing the invention.

22 Claims, No Drawings

POLYMERIZATION CATALYST ACTIVATOR AND ITS USE IN A POLYMERIZATION PROCESS

FIELD OF THE INVENTION

The present invention relates to polymerization catalyst activator compounds, to methods of making these activator compounds, to polymerization catalyst systems containing these activator compounds, and to polymerization processes utilizing the same. More specifically the activator compounds of the invention may be either neutral or ionic and include a Group 13 atom, preferably boron or aluminum, bonded to at least one halogenated or partially halogenated heterocyclic ligand.

BACKGROUND OF THE INVENTION

Polymerization catalyst compounds are typically combined with an activator (or co-catalyst) to yield compositions having a vacant coordination site that will coordinate, insert, and polymerize olefins. Typically, methylaluminoxane (MAO) is utilized to activate metallocene catalysts. Alternative cocatalysts for metallocenes and other single-site polymerization catalysts have been discovered in recent years.

It is known that perfluorophenyl aluminum and borane complexes containing one anionic nitrogen containing group may activate metallocenes. For example, R. E. LaPointe, G. R. Roof, K. A. Abboud, J. Klosin, J. Am. Chem. Soc. 2000, 122, 9560–9561, and WO 01/23442 A1 report the synthesis of (C6F5)3Al(imidazole)Al(C6F5)3][HNR'R"]. In addition, G. Kehr, R. Fröhlich, B. Wibbeling, G. Erker, Chem. Eur. J. 2000, 6, No.2, 258–266 report the synthesis of (N-Pyrrolyl)B(C6F5)2.

SUMMARY OF THE INVENTION

The activator compounds of the invention, in one embodiment, include a cation component and a new coordinating anion component having a Group 13 atom, preferably boron or aluminum, bonded to two or more halogenated or partially halogenated heterocyclic ligands.

In another embodiment, the invention provides for a neutral activator compound including a Group 13 atom, preferably boron or aluminum, bonded to at least two or more halogenated or partially halogenated heterocyclic ligands.

In another embodiment, the halogenated or partially heterocyclic ligands in each of the above embodiments contains one or more heteroatoms selected form Group 15 or 16, preferably the heteroatom(s) is nitrogen, oxygen, or sulfur. The heteroatom groups may be unsubstituted, or one or more positions may be substituted. In a preferred embodiment, one or more positions on the heterocyclic ligand is substituted with a halogen atom or a halogen containing group, where the halogen is preferably fluorine.

In other embodiments, the invention provides for utilizing the above activators in an olefin(s) polymerization process.

DETAILED DESCRIPTION

In one embodiment, the activator compound of the invention includes a cation component capable of reacting with the metal of a polymerization catalyst compound to create a catalytically active transition metal complex, and a new non-coordinating/weakly activator anion component. In another embodiment, the activator compound of the invention is a new neutral activator compound. The new anionic component and the new neutral activator compound of the invention include a Group 13 atom bonded to at least one halogenated or partially halogentated heterocyclic ligand.

For the purposes of this patent specification, term "activator" is used interchangeably with the term "co-catalyst," the term "catalyst" refers to a metal compound that when combined with an activator polymerizes olefins, and the term "catalyst system" refers to the combination of a catalyst, an activator, and an optional support.

In one embodiment, the coordinating anion or the neutral activator of the invention includes a Group 13 atom, preferably boron or aluminum, and more preferably aluminum bonded to at least one halogenated or partially halogenated heterocyclic ligand. Preferably the halogenated or partially heterocyclic ligand contains one or more hetereoatoms selected form Group 15 or 16 of the Period Table of the Elements, more preferably the heteroatom(s) is nitrogen, oxygen, or sulfur and most preferably nitrogen. Non-limiting examples of heterocyclic ligands include pyrrolyl, imidazolyl, pyrazolyl, pyrrolidinyl, purinyl, carbazolyl, and indolyl groups. The heteroatom group may be unsubstituted or one or more positions may be substituted. Preferably, one or more positions on the heterocyclic ligand is substituted with a halogen atom or a halogen containing group, where the halogen is preferably fluorine.

In another embodiment, the coordinating anion of the invention includes a Group 13 atom, preferably boron or aluminum, and more preferably aluminum bonded a nitrogen atom contained in a heterocyclic group where one or more positions on the heterocyclic ligand is substituted with a fluorine atom or a fluorinated group, preferably a fluorinated aryl group, for example a fluorinated phenyl group.

In one embodiment, the activator compound of the invention is an ionic compound represented by Formula (I).

    Formula (I)

In Formula (I), M is a Group 13 atom, preferably boron or aluminum, and more preferably aluminum.

M is bonded to (JY) which represents a heterocyclic group. Y represents the heterocyclic group and J represents at least one heteroatom contained in group Y. M may be bonded to any atom contained in Y, but is preferably bonded to heteroatom J.

Preferably, J is an atom selected from Group 15 or 16 of the Period Table of the Elements, more preferably J is nitrogen, oxygen, or sulfur and most preferably nitrogen.

Non-limiting examples of (JY) include pyrrolyl, imidazolyl, pyrazolyl, pyrrolidinyl, purinyl, carbazolyl, and indolyl groups.

Heterocyclic group (JY) may be unsubstituted or substituted with one or a combination of substituent groups. Examples of suitably substituents include hydrogen, halogen, linear or branched alkyl, alkenyl or alkynyl radicals, cycloalkyl radicals, aryl radicals, aryl substituted alkyl radicals, acyl radicals, aroyl radicals, alkoxy radicals, aryloxy radicals, alkylthio radicals, dialkylamino radicals, alkoxycarbonyl radicals, aryloxycarbonyl radicals, carbomoyl radicals, alkyl- or dialkyl-carbamoyl radicals, acyloxy radicals, acylamino radicals, aroylamino radicals, straight, branched or cyclic, alkylene radicals, or combination thereof. The substituents groups may also be substituted with halogens, particularly fluorine, or heteroatoms or the like.

Non-limiting examples of substituents include methyl, ethyl, propyl, butyl, pentyl, hexyl, cyclopentyl, cyclohexyl, benzyl or phenyl groups and the like, including all their isomers, for example tertiary butyl, isopropyl, and the like. Other examples of substituents include fluoromethyl, fluroethyl, difluroethyl, iodopropyl, bromohexyl, chlorobenzyl.

Preferably one or more positions on the heterocyclic group (JY) is substituted with a halogen atom or a halogen atom containing group, preferably the halogen is fluorine. More preferably, the substituent is a fluorine atom or a fluorinated aryl group such as a fluorinated phenyl group.

x is the valence of M+1.

The cation component, (Cat)$^+$ may include Bronsted acids such as protons or protonated Lewis bases or reducible Lewis acids capable of protonating or abstracting a moiety, such as an alkyl or aryl group, from the catalyst precursor compound, resulting in a cationic transition metal species.

The activating cation (Cat)$^+$ may be a Bronsted acid, capable of donating a proton to the catalyst precursor resulting in a transition metal cation, including ammonium, oxonium, phosphonium, silylium species, and mixtures thereof, preferably ammonium species derived from methylamine, aniline, dimethylamine, diethylamine, N-methylaniline, diphenylamine, trimethylamine, triethylamine, N,N-dimethylaniline, methyldiphenylamine, pyridine, p-bromo-N,N-dimethylaniline and p-nitro-N,N-dimethylaniline; phosphonium species derived from triethylphosphine, triphenylphosphine, and diphenylphosphine; oxonium species derived from ethers such as dimethyl ether, diethyl ether, tetrahydrofuran and dioxane; sulfonium species derived from thioethers, such as diethyl thioether and tetrahydrothiophene; and mixtures thereof. The activating cation (Cat)$^+$ may also be an abstracting moiety such as a silver, carbonium, tropylium, carbenium, ferrocenium species and mixtures thereof, preferably carbonium or ferrocenium species, and is preferably triphenylcarbonium. In a most preferred embodiment, the cation component is a dimethylanilinium cation.

In a preferred embodiment, in Formula (I) M is Al or B, preferably Al, J is a nitrogen atom bonded to M and contained in a heterocyclic group Y where one or more positions on the heterocyclic ligand is substituted with a fluorine atom. More preferably, Y is a fluorinated or partially fluorinated indolyl group and Cat$^+$ is a dimethylanilinium cation.

In another embodiment, the activator compound of the invention is a neutral compound represented by Formula (II).

M(JY)$_x$            Formula (II)

In Formula (II), M and (JY) are defined as above for Formula (I) and x is the valence of M.

In another embodiment, each (JY) of Formulae (I) and (II) is independently represented by Formula (III)

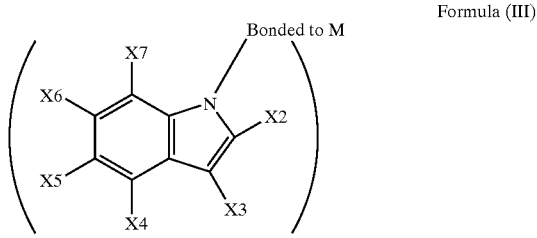

Formula (III)

In Formula (III), and referring to Formulae (I) and (II) J is a nitrogen atom bonded to M, x is the valence of M or the valence of M+1, and Y is an indolyl group having substituents X2–X7. Each X2–X7 is independently selected from hydrogen, halogen, preferably fluorine, an alkyl group, an aryl group, an alkoxide group, an aryloxide group or an alkyl substituted aryl group. Preferably, Each X2–X7 is independently hydrogen, halogen, an alkyl group, a halogenated or partially halogenated alkyl group, an aryl group, a halogenated or partially halogenated aryl group, an aryl substituted alkyl group or a halogenated or partially halogenated aryl substituted alkyl group. Preferably the halogen is fluorine. More preferably, each of X2 and X4–X7 are independently hydrogen, halogen, preferably fluorine, an alkyl, a halogenated or partially halogenated group alkyl group, an aryl group, or a halogenated or partially halogenated aryl group, and X3 is hydrogen, a halogenated or partially halogenated aryl group, an aryl substituted alkyl group, or a halogenated or partially halogenated aryl substituted alkyl group. More preferably X3 is a halogenated or partially halogenated phenyl group. More preferably each of X4–X7 is a fluoride atom.

In a particular preferred embodiment, the activator complex of the invention is represented the Structures (I)–(IV) below. Although pictured with DMAH as the cation, it is understood that the non-coordinating, weakly coordinating anion of the invention may be utilized with any suitable cation.

Structure (I)

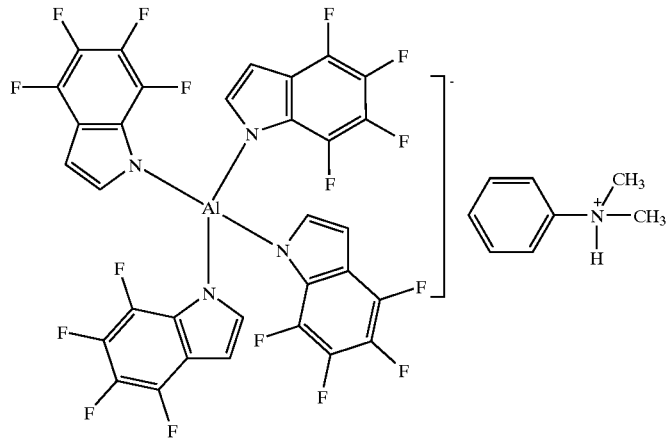

Structure (II)
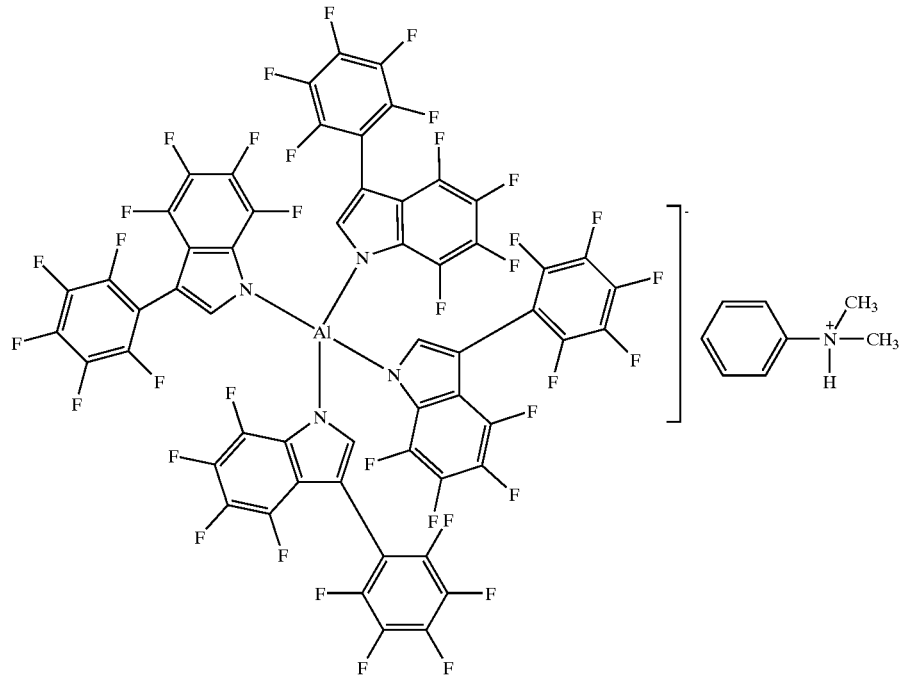
Structure (III)
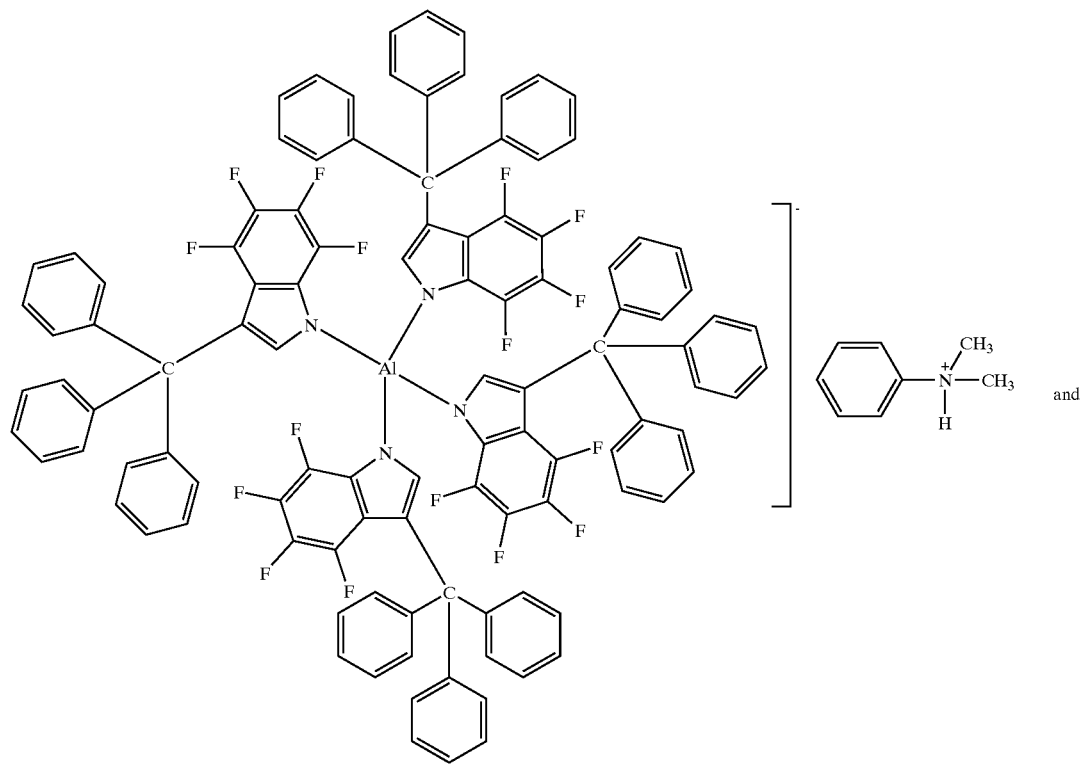
and

Structure (IV)

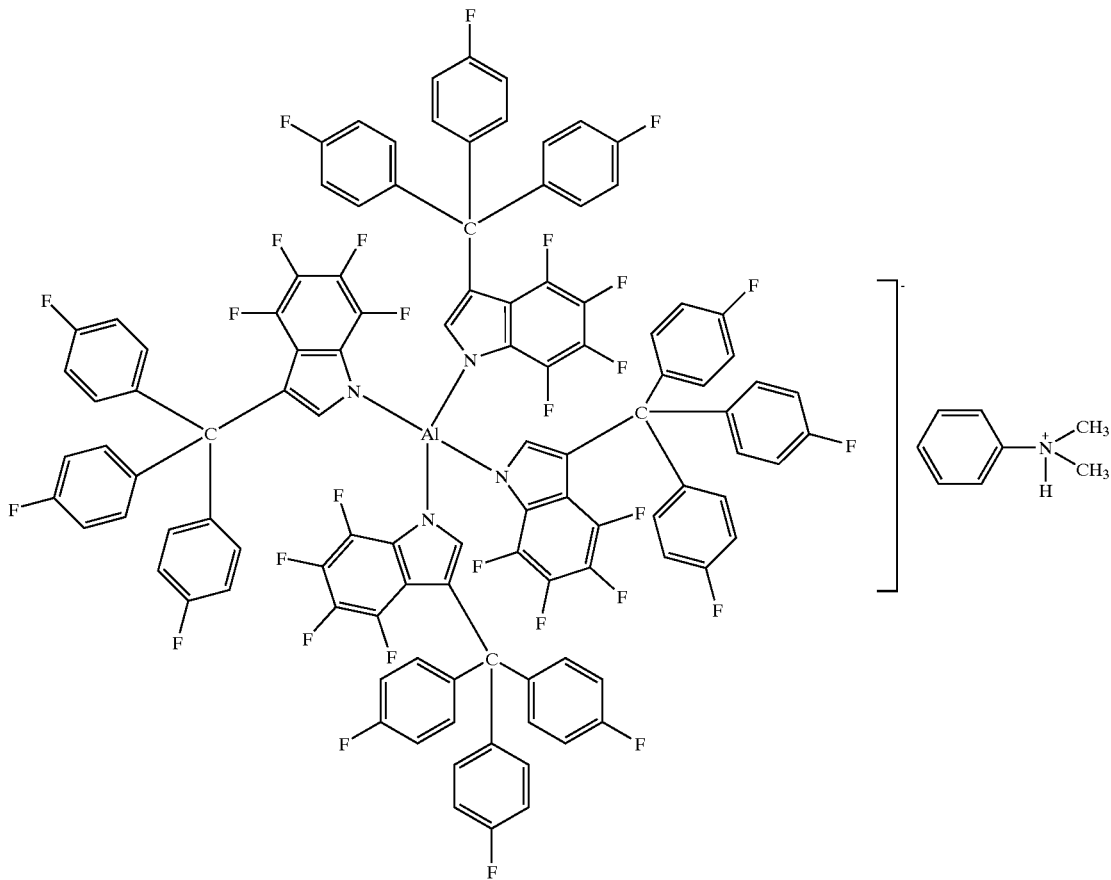

In another embodiment, one or more of the activators of the invention may be used in combination with each other or in combination with other activators or methods of activation. For example, the activators of the invention may be used in combination with other activators including aluminoxane, modified aluminoxane, tri (n-butyl) ammonium tetrakis (pentafluorophenyl) boron, a trisperfluorophenyl boron metalloid precursor or a trisperfluoronapthyl boron metalloid precursor, polyhalogenated heteroborane anions, trimethylaluminum, triethylaluminum, triisobutylaluminum, tri-n-hexylaluminum, tri-n-octylaluminum, tris(2,2',2"-nona-fluorobiphenyl) fluoroaluminate, perchlorates, periodates, iodates and hydrates, (2,2'-bisphenyl-ditrimethylsilicate)#4THF and organo-boron-aluminum compound, silylium salts and dioctadecylmethylammonium-bis(tris(pentafluorophenyl)borane)-benzimidazolide or combinations thereof.

The activator compounds described above may be prepared by methods known in the art. For example, a heterocyclic compound, such as an indole, may be dissolved in an appropriate solvent and deprotonated with a base such as n-butyl lithium or potassium hydride. This reaction is typically performed in diethyl ether or tetrahydrofuran. The lithium or potassium salt may be isolated and further reacted in situ with an aluminum reagent such as aluminum trichloride. The tetrakis aluminate salt may then be isolated or further reacted with an "activating" source such as dimethylanilinium chloride in a suitable solvent such as dichloromethane.

Catalyst Compositions

The activator complexes of the invention may be utilized in conjunction with any suitable polymerization catalyst compound or compounds to polymerize olefin(s). Examples of suitable catalyst compounds include bulky ligand metallocene catalyst compositions, Group 15 containing metal polymerization catalyst compositions, and phenoxide transition metal catalyst compositions. The following is a non-limiting discussion of the various polymerization catalysts which may be utilized with the activator complex of this invention.

Bulky Ligand Metallocene Catalyst Compositions

The activator complexes of the present invention may be used to activate bulky ligand metallocene catalyst compositions. Generally, these catalyst compounds include half and full sandwich compounds having one or more bulky ligands bonded to at least one metal atom. Typical bulky ligand metallocene compounds are described as containing one or more bulky ligand(s) and one or more leaving group(s) bonded to at least one metal atom.

The bulky ligands are generally represented by one or more open, acyclic, or fused ring(s) or ring system(s) or a combination thereof. The ring(s) or ring system(s) of these bulky ligands are typically composed of atoms selected from Groups 13 to 16 atoms of the Periodic Table of the Elements. Preferably the atoms are selected from the group consisting of carbon, nitrogen, oxygen, silicon, sulfur, phosphorous, germanium, boron and aluminum or a combination thereof. Most preferably the ring(s) or ring system(s) are composed of carbon atoms such as but not limited to those cyclopentadienyl ligands or cyclopentadienyl-type ligand structures or other similar functioning ligand structure such as a pentadiene, a cyclooctatetraendiyl or an imide ligand. The metal atom is preferably selected from Groups 3 through 15 and the lanthanide or actinide series of the Periodic Table of the Elements. Preferably the metal is a transition metal from Groups 4 through 12, more preferably Groups 4, 5 and 6, and most preferably the transition metal is from Group 4.

In one embodiment, the bulky ligand metallocene catalyst compounds, which may be utilized with the activator complex of the invention, may be represented by Formula (IV):

$$L^A L^B MQ_n \qquad \text{Formula (IV)}$$

where M is a metal atom from the Periodic Table of the Elements and may be a Group 3 to 12 metal or from the lanthanide or actinide series of the Periodic Table of the Elements, preferably M is a Group 4, 5 or 6 transition metal, more preferably M is zirconium, hafnium or titanium. The bulky ligands, $L^A$ and $L^B$, are open, acyclic or fused ring(s) or ring system(s) and are any ancillary ligand system, including unsubstituted or substituted, cyclopentadienyl ligands or cyclopentadienyl-type ligands, heteroatom substituted and/or heteroatom containing cyclopentadienyl-type ligands. Non-limiting examples of bulky ligands include cyclopentadienyl ligands, cyclopentaphenanthreneyl ligands, indenyl ligands, benzindenyl ligands, fluorenyl ligands, octahydrofluorenyl ligands, cyclooctatetraendiyl ligands, cyclopentacyclododecene ligands, azenyl ligands, azulene ligands, pentalene ligands, phosphoyl ligands, phosphinimine (WO 99/40125), pyrrolyl ligands, pyrozolyl ligands, carbazolyl ligands, borabenzene ligands and the like, including hydrogenated versions thereof, for example tetrahydroindenyl ligands. In another embodiment, $L^A$ and $L^B$ may comprise one or more heteroatoms, for example, nitrogen, silicon, boron, germanium, sulfur and phosphorous, in combination with carbon atoms to form an open, acyclic, or preferably a fused, ring or ring system, for example, a hetero-cyclopentadienyl ancillary ligand. Other $L^A$ and $L^B$ bulky ligands include but are not limited to bulky amides, phosphides, alkoxides, aryloxides, imides, carbolides, borollides, porphyrins, phthalocyanines, corrins and other polyazomacrocycles. Independently, each $L^A$ and $L^B$ may be the same or different type of bulky ligand that is bonded to M. In one embodiment of Formula (IV) only one of either $L^A$ or $L^B$ is present.

Independently, each $L^A$ and $L^B$ may be unsubstituted or substituted with a combination of substituent groups R. Non-limiting examples of substituent groups R include one or more from the group selected from hydrogen, or linear, branched alkyl radicals, or alkenyl radicals, alkynyl radicals, cycloalkyl radicals or aryl radicals, acyl radicals, aroyl radicals, alkoxy radicals, aryloxy radicals, alkylthio radicals, dialkylamino radicals, alkoxycarbonyl radicals, aryloxycarbonyl radicals, carbomoyl radicals, alkyl- or dialkylcarbamoyl radicals, acyloxy radicals, acylamino radicals, aroylamino radicals, straight, branched or cyclic, alkylene radicals, or combination thereof. In a preferred embodiment, substituent groups R have up to 50 non-hydrogen atoms, preferably from 1 to 30 carbon, that can also be substituted with halogens or heteroatoms or the like. Non-limiting examples of alkyl substituents R include methyl, ethyl, propyl, butyl, pentyl, hexyl, cyclopentyl, cyclohexyl, benzyl or phenyl groups and the like, including all their isomers, for example tertiary butyl, isopropyl, and the like. Other hydrocarbyl radicals include fluoromethyl, fluroethyl, difluroethyl, iodopropyl, bromohexyl, chlorobenzyl and hydrocarbyl substituted organometalloid radicals including trimethylsilyl, trimethylgermyl, methyldiethylsilyl and the like; and halocarbyl-substituted organometalloid radicals including tris(trifluoromethyl)-silyl, methyl-bis (difluoromethyl)silyl, bromomethyldimethylgermyl and the like; and disubstitiuted boron radicals including dimethylboron for example; and disubstituted pnictogen radicals including dimethylamine, dimethylphosphine, diphenylamine, methylphenylphosphine, chalcogen radicals including methoxy, ethoxy, propoxy, phenoxy, methylsulfide and ethylsulfide. Non-hydrogen substituents R include the atoms carbon, silicon, boron, aluminum, nitrogen, phosphorous, oxygen, tin, sulfur, germanium and the like, including olefins such as but not limited to olefinically unsaturated substituents including vinyl-terminated ligands, for example but-3-enyl, prop-2enyl, hex-5-enyl and the like. Also, at least two R groups, preferably two adjacent R groups, are joined to form a ring structure having from 3 to 30 atoms selected from carbon, nitrogen, oxygen, phosphorous, silicon, germanium, aluminum, boron or a combination thereof. Also, a substituent group R group such as 1-butanyl may form a carbon sigma bond to the metal M.

Other ligands may be bonded to the metal M, such as at least one leaving group Q. For the purposes of this patent specification and appended claims the term "leaving group" is any ligand that can be abstracted from a bulky ligand metallocene catalyst compound to form a bulky ligand metallocene catalyst cation capable of polymerizing one or more olefin(s). In one embodiment, Q is a monoanionic labile ligand having a sigma-bond to M. Depending on the oxidation state of the metal, the value for n is 0, 1 or 2 such that Formula (IV) above represents a neutral bulky ligand metallocene catalyst compound.

Non-limiting examples of Q ligands include weak bases such as amines, phosphines, ethers, carboxylates, dienes, hydrocarbyl radicals having from 1 to 20 carbon atoms, hydrides or halogens and the like or a combination thereof. In another embodiment, two or more Q's form a part of a fused ring or ring system. Other examples of Q ligands include those substituents for R as described above and including cyclobutyl, cyclohexyl, heptyl, tolyl, trifluromethyl, tetramethylene, pentamethylene, methylidene, methyoxy, ethyoxy, propoxy, phenoxy, bis(N-methylanilide), dimethylamide, dimethylphosphide radicals and the like.

In another embodiment, the activator complex of the invention is utilized with the bulky ligand metallocene catalyst compounds of Formula (V) where $L^A$ and $L^B$ are bridged to each other by at least one bridging group, A, as represented in the following formula:

$$L^A AL^B MQ_n \qquad \text{Formula (V)}$$

These bridged compounds represented by Formula (V) are known as bridged, bulky ligand metallocene catalyst compounds. $L^A$, $L^B$, M, Q and n are as defined above. Non-limiting examples of bridging group A include bridging groups containing at least one Group 13 to 16 atom, often referred to as a divalent moiety such as but not limited to at least one of a carbon, oxygen, nitrogen, silicon, aluminum, boron, germanium and tin atom or a combination thereof. Preferably bridging group A contains a carbon, silicon or germanium atom, most preferably A contains at least one silicon atom or at least one carbon atom. The bridging group A may also contain substituent groups R as defined above including halogens and iron. Non-limiting examples of bridging group A may be represented by $R'_2C$, $R'_2Si$, $R'_2Si$ $R'_2Si$, $R'_2Ge$, $R'P$, where R' is independently, a radical group which is hydride, hydrocarbyl, substituted hydrocarbyl, halocarbyl, substituted halocarbyl, hydrocarbyl-substituted organometalloid, halocarbyl-substituted organometalloid, disubstituted boron, disubstituted pnictogen, substituted chalcogen, or halogen or two or more R' may be joined to form a ring or ring system. In one embodiment, the bridged, bulky ligand metallocene catalyst compounds of Formula (V) have two or more bridging groups A (EP 664 301 B1).

In another embodiment, the activator complex of the invention may be utilized with bulky ligand metallocene catalyst compounds where the R substituents on the bulky ligands $L^A$ and $L^B$ of Formulas (IV) and (V) are substituted with the same or different number of substituents on each of the bulky ligands. In another embodiment, the bulky ligands $L^A$ and $L^B$ of formulas (IV) and (V) are different from each other.

In another embodiment, the activator complex of the invention may be utilized with other bulky ligand metallocene catalyst compounds such as those described in U.S. Pat. Nos. 5,064,802, 5,145,819, 5,149,819, 5,243,001, 5,239,022, 5,276,208, 5,296,434, 5,321,106, 5,329,031, 5,304,614, 5,677,401, 5,723,398, 5,753,578, 5,854,363, 5,856,547 5,858,903, 5,859,158, 5,900,517 and 5,939,503 and PCT publications WO 93/08221, WO 93/08199, WO 95/07140, WO 98/11144, WO 98/41530, WO 98/41529, WO 98/46650, WO 99/02540 and WO 99/14221 and European publications EP-A-0 578 838, EP-A-0 638 595, EP-B-0 513 380, EP-A1-0 816 372, EP-A2-0 839 834, EP-B1-0 632 819, EP-B1-0 748 821 and EP-B1-0 757 996, all of which are fully incorporated herein by reference.

In another embodiment, the activator complex of the invention may be utilized with bulky ligand metallocene catalysts which include bridged heteroatom, mono-bulky ligand metallocene compounds. These types of catalysts and catalyst systems are described in, for example, PCT publication WO 92/00333, WO 94/07928, WO 91/04257, WO 94/03506, WO 96/00244, WO 97/15602 and WO 99/20637 and U.S. Pat. Nos. 5,057,475, 5,096,867, 5,055,438, 5,198,401, 5,227,440 and 5,264,405 and European publication EP-A-0 420 436, all of which are herein fully incorporated by reference.

In this embodiment, the activator complexes of the invention are utilized with a bulky ligand metallocene catalyst compound represented by Formula (VI):

$$L^C AJMQ_n \qquad \text{Formula (VI)}$$

where M is a Group 3 to 16 metal atom or a metal selected from the Group of actinides and lanthanides of the Periodic Table of the Elements, preferably M is a Group 4 to 12 transition metal, and more preferably M is a Group 4, 5 or 6 transition metal, and most preferably M is a Group 4 transition metal in any oxidation state, especially titanium; $L^C$ is a substituted or unsubstituted bulky ligand bonded to M; J is bonded to M; A is bonded to $L^C$ and J; J is a heteroatom ancillary ligand; and A is a bridging group; Q is a univalent anionic ligand; and n is the integer 0,1 or 2. In Formula (VI) above, $L^C$, A and J form a fused ring system. In an embodiment, $L^C$ of formula (VI) is as defined above for $L^A$, A, M and Q of formula (VI) are as defined above in formula (V).

In Formula (VI) J is a heteroatom containing ligand in which J is an element with a coordination number of three from Group 15 or an element with a coordination number of two from Group 16 of the Periodic Table of the Elements. Preferably J contains a nitrogen, phosphorus, oxygen or sulfur atom with nitrogen being most preferred.

In another embodiment, the activator complex of the invention is utilized with a bulky ligand metallocene catalyst compound which is a complex of a metal, preferably a transition metal, a bulky ligand, preferably a substituted or unsubstituted pi-bonded ligand, and one or more heteroallyl moieties, such as those described in U.S. Pat. Nos. 5,527,752 and 5,747,406 and EP-B1-0 735 057, all of which are herein fully incorporated by reference.

In another embodiment, the activator complex of the invention is utilized with a ligand metallocene catalyst compound which may be represented by Formula (VII):

$$L^D MQ_2(YZ)X_n \qquad \text{Formula (VII)}$$

where M is a Group 3 to 16 metal, preferably a Group 4 to 12 transition metal, and most preferably a Group 4, 5 or 6 transition metal; $L^D$ is a bulky ligand that is bonded to M; each Q is independently bonded to M and $Q_2$(YZ) forms a unicharged polydentate ligand; A or Q is a univalent anionic ligand also bonded to M; X is a univalent anionic group when n is 2 or X is a divalent anionic group when n is 1; n is 1 or 2.

In Formula (VII), L and M are as defined above for Formula (IV). Q is as defined above for Formula (IV), preferably Q is selected from the group consisting of —O—, —NR—, —CR$_2$— and —S—; Y is either C or S; Z is selected from the group consisting of —OR, —NR$_2$, —CR$_3$, —SR, —SiR$_3$, —PR$_2$, —H, and substituted or unsubstituted aryl groups, with the proviso that when Q is —NR— then Z is selected from one of the group consisting of —OR, —NR$_2$, —SR, —SiR$_3$, —PR$_2$ and —H; R is selected from a group containing carbon, silicon, nitrogen, oxygen, and/or phosphorus, preferably where R is a hydrocarbon group containing from 1 to 20 carbon atoms, most preferably an alkyl, cycloalkyl, or an aryl group; n is an integer from 1 to 4, preferably 1 or 2; X is a univalent anionic group when n is 2 or X is a divalent anionic group when n is 1; preferably X is a carbamate, carboxylate, or other heteroallyl moiety described by the Q, Y and Z combination.

In another embodiment, the activator complex of the invention is utilized with a bulky ligand metallocene catalyst compounds, which include heterocyclic ligand complexes where the bulky ligands, the ring(s) or ring system(s), include one or more heteroatoms or a combination thereof. Non-limiting examples of heteroatoms include a Group 13 to 16 element, preferably nitrogen, boron, sulfur, oxygen, aluminum, silicon, phosphorous and tin. Examples of these bulky ligand metallocene catalyst compounds are described in WO 96/33202, WO 96/34021, WO 97/17379 and WO 98/22486 and EP-A1-0 874 005 and U.S. Pat. Nos. 5,637,660, 5,539,124, 5,554,775, 5,756,611, 5,233,049, 5,744,417, and 5,856,258 all of which are herein incorporated by reference.

In another embodiment, the activator complex of the invention may be utilized with bulky ligand metallocene catalyst compounds, which include complexes known as transition metal catalysts based on bidentate ligands containing pyridine or quinoline moieties, such as those described in U.S. application Ser. No. 09/103,620 filed Jun. 23, 1998, which is herein incorporated by reference. In another embodiment, the bulky ligand metallocene catalyst compounds are those described in PCT publications WO 99/01481 and WO 98/42664, which are fully incorporated herein by reference.

In another embodiment, the activator complex of the invention may be utilized with a bulky ligand metallocene catalyst compounds which may be represented by Formula (VIII):

$$((Z)XA_t(YJ))_q MQ_n \qquad \text{Formula (VIII)}$$

where M is a metal selected from Group 3 to 13 or lanthanide and actinide series of the Periodic Table of the Elements; Q is bonded to M and each Q is a monovalent, bivalent, or trivalent anion; X and Y are bonded to M; one or more of X and Y are heteroatoms, preferably both X and Y are heteroatoms; Y is contained in a heterocyclic ring J, where J comprises from 2 to 50 non-hydrogen atoms, preferably 2 to 30 carbon atoms; Z is bonded to X, where Z comprises 1 to 50 non-hydrogen atoms, preferably 1 to 50 carbon atoms, preferably Z is a cyclic group containing 3 to 50 atoms, preferably 3 to 30 carbon atoms; t is 0 or 1; when t is 1, A is a bridging group joined to at least one of X, Y or J, preferably X and J; q is 1 or 2; n is an integer from 1 to 4 depending on the oxidation state of M. In one embodiment, where X is oxygen or sulfur then Z is optional. In another embodiment, where X is nitrogen or phosphorous then Z is present. In an embodiment, Z is preferably an aryl group, more preferably a substituted aryl group.

It is also within the scope of this invention, in one embodiment, that the bulky ligand metallocene catalyst compounds, which may be utilized with the activator complex of the invention include complexes of $Ni^{2+}$ and $Pd^{2+}$ described in the articles Johnson, et al., "New Pd(II)- and Ni(II)-Based Catalysts for Polymerization of Ethylene and a-Olefins", J. Am. Chem. Soc. 1995, 117, 6414–6415 and Johnson, et al., "Copolymerization of Ethylene and Propylene with Functionalized Vinyl Monomers by Palladium(II) Catalysts", J. Am. Chem. Soc., 1996, 118, 267–268, and WO 96/23010 published Aug. 1, 1996, WO 99/02472, U.S. Pat. Nos. 5,852,145, 5,866,663 and 5,880,241, which are all herein fully incorporated by reference. These complexes can be either dialkyl ether adducts, or alkylated reaction products of the described dihalide complexes that can be activated to a cationic state by the activators of this invention described below.

Also included as bulky ligand metallocene catalyst are those diimine based ligands of Group 8 to 10 metal compounds disclosed in PCT publications WO 96/23010 and WO 97/48735 and Gibson, et al., Chem. Comm., pp. 849–850 (1998), all of which are herein incorporated by reference.

Other bulky ligand metallocene catalysts, which may be utilized with the activator complex of the invention, are those Group 5 and 6 metal imido complexes described in EP-A2-0 816 384 and U.S. Pat. No. 5,851,945, which is incorporated herein by reference. In addition, bridged bis (amido) catalyst compounds are described in WO 96/27439, which is herein incorporated by reference. Other bulky ligand metallocene catalysts are described as bis(hydroxy aromatic nitrogen ligands) in U.S. Pat. No. 5,852,146, which is incorporated herein by reference. Other metallocene catalysts containing one or more Group 15 atoms include those described in WO 98/46651, which is herein incorporated herein by reference. Still another metallocene bulky ligand metallocene catalysts include those multinuclear bulky ligand metallocene catalysts as described in WO 99/20665, which is incorporated herein by reference.

It is also contemplated that in one embodiment, the bulky ligand metallocene catalysts of the invention described above include their structural or optical or enantiomeric isomers (meso and racemic isomers, for example see U.S. Pat. No. 5,852,143, incorporated herein by reference) and mixtures thereof.

Group 15 Containing Polymerization Catalyst

The activator complexes of the invention may also be utilized with metal containing Group 15 polymerization catalyst compounds. Generally, these catalysts includes a Group 3 to 14 metal atom, preferably a Group 3 to 7, more preferably a Group 4 to 6, and even more preferably a Group 4 metal atom, bound to at least one leaving group and also bound to at least two Group 15 atoms, at least one of which is also bound to a Group 15 or 16 atom through another group.

Preferably, at least one of the Group 15 atoms is also bound to a Group 15 or 16 atom through another group which may be a $C_1$ to $C_{20}$ hydrocarbon group, a heteroatom containing group, silicon, germanium, tin, lead, or phosphorus, wherein the Group 15 or 16 atom may also be bound to nothing or a hydrogen, a Group 14 atom containing group, a halogen, or a heteroatom containing group, and wherein each of the two Group 15 atoms are also bound to a cyclic group and may optionally be bound to hydrogen, a halogen, a heteroatom or a hydrocarbyl group, or a heteroatom containing group.

In another embodiment of the invention the composition containing alternating atoms of Group 14 and Group 16 may be used to create solutions or emulsions including one or more bulky ligand metallocene catalyst compounds, and one or more conventional-type catalyst compounds or catalyst systems. Non-limiting examples of mixed catalysts and catalyst systems are described in U.S. Pat. Nos. 4,159,965, 4,325,837, 4,701,432, 5,124,418, 5,077,255, 5,183,867, 5,391,660, 5,395,810, 5,691,264, 5,723,399 and 5,767,031 and PCT Publication WO 96/23010 published Aug. 1, 1996, all of which are herein fully incorporated by reference.

Metal containing Group 15 catalyst compounds may be represented by Formulae (IX) or (X):

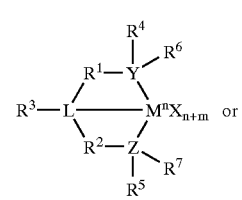

Formula (IX)

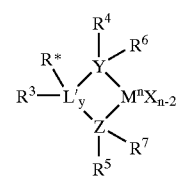

Formula (X)

wherein M is a transition metal, preferably a Group 3 to 14 main group metal, preferably a Group 4, 5, or 6 metal, and more preferably a Group 4 metal, and most preferably zirconium, titanium or hafnium, each X is independently a leaving group, preferably an anionic leaving group, and more preferably hydrogen, a hydrocarbyl group, a heteroatom, or a halogen, and most preferably an alkyl or an aryl substituted alkyl.

y is 0 or 1 (when y is 0 group L' is absent), n is the oxidation state of M, preferably +3, +4, or +5, and more preferably +4, m is the formal charge of the YZL or the YZL' ligand, preferably 0, −1, −2 or −3, and more preferably −2, L is a Group 15 or 16 element, preferably nitrogen, L' is a Group 15 or 16 element or Group 14 containing group, preferably carbon, silicon or germanium, Y is a Group 15 element, preferably nitrogen or phosphorus, and more preferably nitrogen, Z is a Group 15 element, preferably nitrogen or phosphorus, and more preferably nitrogen, $R^1$ and $R^2$ are independently a $C_1$ to $C_{20}$ hydrocarbon group, a heteroatom containing group having up to twenty carbon atoms, silicon, germanium, tin, lead, or phosphorus, preferably a $C_2$ to $C_{20}$ alkyl, aryl or aralkyl group, more preferably a linear, branched or cyclic $C_2$ to $C_{20}$ alkyl group, most preferably a $C_2$ to $C_6$ hydrocarbon group.

$R^3$ is absent, a hydrocarbon group, hydrogen, a halogen, a heteroatom containing group, preferably a linear, cyclic or branched alkyl group having 1 to 20 carbon atoms, more preferably $R^3$ is absent, hydrogen or an alkyl group, and most preferably hydrogen.

$R^4$ and $R^5$ are independently an alkyl group, an aryl group, substituted aryl group, a cyclic alkyl group, a substituted cyclic alkyl group, a cyclic aralkyl group, a substituted cyclic aralkyl group or a multiple ring system, preferably having up to 20 carbon atoms, more preferably between 3 and 10 carbon atoms, and even more preferably a $C_1$ to $C_{20}$ hydrocarbon group, a $C_1$ to $C_{20}$ aryl group or a $C_1$ to $C_{20}$ aralkyl group, or a heteroatom containing group, for example $PR_3$, where R is an alkyl group, $R^1$ and $R^2$ may be interconnected to each other, and/or $R^4$ and $R^5$ may be interconnected to each other, $R^6$ and $R^7$ are independently absent, or hydrogen, an alkyl group, halogen, heteroatom or a hydrocarbyl group, preferably a linear, cyclic or branched alkyl group having 1 to 20 carbon atoms, more preferably absent, and $R^+$ is absent, or is hydrogen, a Group 14 atom containing group, a halogen, a heteroatom containing group.

By "formal charge of the YZL or YZL' ligand", it is meant the charge of the entire ligand absent the metal and the leaving groups X. By "$R^1$ and $R^2$ may also be interconnected" it is meant that $R^1$ and $R^2$ may be directly bound to each other or may be bound to each other through other groups. By "$R^4$ and $R^5$ may also be interconnected" it is meant that $R^4$ and $R^5$ may be directly bound to each other or may be bound to each other through other groups.

Phenoxide Transition Metal Catalyst Compositions

The activator complexes of the invention may also be used with phenoxide transition metal catalyst compounds. Generally, these complexes are heteroatom substituted phenoxide ligated Group 3 to 10 transition metal or lanthanide metal compounds wherein the metal is bound to the oxygen of the phenoxide group.

Phenoxide transition metal catalyst compounds may be represented by Formulae XI or XII:

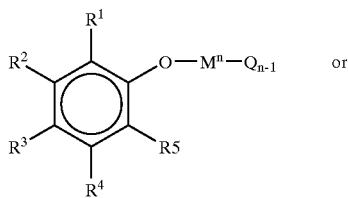

Formula (XI)

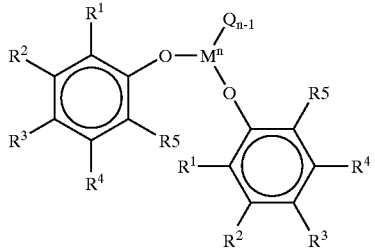

Formula (XII)

wherein $R^1$ is hydrogen or a $C_4$ to $C_{100}$ group, preferably a tertiary alkyl group, preferably a $C_4$ to $C_{20}$ alkyl group, preferably a $C_4$ to $C_{20}$ tertiary alkyl group, preferably a neutral $C_4$ to $C_{100}$ group and may or may not also be bound to M;

at least one of $R^2$ to $R^5$ is a heteroatom containing group, the rest of $R^2$ to $R^5$ are independently hydrogen or a $C_1$ to $C_{100}$ group, preferably a $C_4$ to $C_{20}$ alkyl group, preferred examples of which include butyl, isobutyl, t-butyl, pentyl, hexyl, heptyl, isohexyl, octyl, isooctyl, decyl, nonyl, dodecyl, and any of $R^2$ to $R^5$ also may or may not be bound to M;

Each $R^1$ to $R^5$ group may be independently substituted or unsubstituted with other atoms, including heteroatoms or heteroatom containing group(s);

O is oxygen;

M is a Group 3 to Group 10 transition metal or lanthanide metal, preferably a Group 4 metal, preferably M is Ti, Zr or Hf;

n is the valence state of the metal M, preferably 2, 3, 4, or 5; and

Q is, and each Q may be independently be, an alkyl, halogen, benzyl, amide, carboxylate, carbamate, thiolate, hydride or alkoxide group, or a bond to an R group containing a heteroatom which may be any of $R^1$ to $R^5$.

A heteroatom containing group may be any heteroatom or a heteroatom bound to carbon, silicon or another heteroatom. Preferred heteroatoms include boron, aluminum, silicon, nitrogen, phosphorus, arsenic, tin, lead, antimony, oxygen, selenium, tellurium. Particularly preferred heteroatoms include nitrogen, oxygen, phosphorus, and sulfur. Even more particularly preferred heteroatoms include nitrogen and oxygen. The heteroatom itself may be directly bound to the phenoxide ring or it may be bound to another atom or atoms that are bound to the phenoxide ring. The heteroatom containing group may contain one or more of the same or different heteroatoms. Preferred heteroatom containing groups include imines, amines, oxides, phosphines, ethers, ketones, oxoazolines heterocyclics, oxazolines, thioethers, and the like. Particularly preferred heteroatom containing groups include imines. Any two adjacent R groups may form a ring structure, preferably a 5 or 6 membered ring. Likewise the R groups may form multi-ring structures. In one embodiment any two or more R groups do not form a 5 membered ring.

In a preferred embodiment the heteroatom substituted phenoxide transition metal compound is an iminophenoxide Group 4 transition metal compound, and more preferably an iminophenoxidezirconium compound.

Other Bulky Ligand Metallocene Catalyst Compounds

Other catalysts are those Group 5 and 6 metal imido complexes described in EP-A2-0 816 384 and U.S. Pat. No. 5,851,945, which is incorporated herein by reference. In addition, other catalysts include bridged bis(arylamido) Group 4 compounds described by D. H. McConville, et al., in Organometallics 1195, 14, 5478–5480, which is herein incorporated by reference. Bridged bis(amido) catalyst compounds are described in WO 96/27439, which is herein incorporated by reference may also be activated by the compositions of the present invention. Other suitable catalysts are described as bis(hydroxy aromatic nitrogen ligands) in U.S. Pat. No. 5,852,146, which is incorporated herein by reference. Other catalysts containing one or more Group 15 atoms include those described in WO 98/46651, which is herein incorporated herein by reference. Still another catalysts include those multinuclear bulky ligand metallocene catalysts as described in WO 99/20665, which is incorporated herein by reference.

It is also contemplated that in one embodiment, the activator complexes of the inventions are utilized with bulky ligand metallocene catalysts including their structural or optical or enantiomeric isomers (meso and racemic isomers, for example see U.S. Pat. No. 5,852,143, incorporated herein by reference) and mixtures thereof.

In another embodiment, it is further contemplated that the polymerization catalysts, described above may be used in combination with the activator(s) of the present invention.

In one embodiment, the mole ratio of the metal of the activator component of the invention to the metal component is preferably in the range of ratios of between 0.3:1 to 3:1.

Supports, Carriers and General Supporting Techniques

The activator complexes of the invention and/or the polymerization catalyst compound may be combined with one or more support materials or carriers, using one of the support methods known in the art or as described below. For example, in one embodiment the activator complex is in a supported form, for example deposited on, contacted with, vaporized with, bonded to, or incorporated within, adsorbed or absorbed in, or on, a support or carrier. In another embodiment, the activator and a catalyst compound may be deposited on, contacted with, vaporized with, bonded to, or incorporated within, adsorbed or absorbed in, or on, a support or carrier.

The terms "support" or "carrier", for purposes of this patent specification, are used interchangeably and are any support material, preferably a porous support material, including inorganic or organic support materials. Non-limiting examples of inorganic support materials include inorganic oxides and inorganic chlorides. Other carriers include resinous support materials such as polystyrene, functionalized or crosslinked organic supports, such as polystyrene, divinyl benzene, polyolefins, or polymeric compounds, zeolites, talc, clays, or any other organic or inorganic support material and the like, or mixtures thereof.

The preferred carriers are inorganic oxides that include those Group 2, 3, 4, 5, 13 or 14 metal oxides. The preferred supports include silica, alumina, silica-alumina, magnesium chloride, and mixtures thereof. Other useful supports include magnesia, titania, zirconia, montmorillonite (EP-B1 0 511 665), phyllosilicate, and the like. Also, combinations of these support materials may be used, for example, silica-chromium, silica-alumina, silica-titania and the like. Additional support materials may include those porous acrylic polymers described in EP 0 767 184 B1, which is incorporated herein by reference.

It is preferred that the carrier, most preferably an inorganic oxide, has a surface area in the range of from about 10 to about 700 m$^2$/g, pore volume in the range of from about 0.1 to about 4.0 cc/g and average particle size in the range of from about 5 to about 500 µm. More preferably, the surface area of the carrier is in the range of from about 50 to about 500 m$^2$/g, pore volume of from about 0.5 to about 3.5 cc/g and average particle size of from about 10 to about 200 µm. Most preferably the surface area of the carrier is in the range is from about 100 to about 400 m$^2$/g, pore volume from about 0.8 to about 3.0 cc/g and average particle size is from about 5 to about 100 µm. The average pore size of the carrier of the invention typically has pore size in the range of from 10 to 1000 Å, preferably 50 to about 500 Å, and most preferably 75 to about 350 Å.

Examples of supporting bulky ligand metallocene-type catalyst systems, which may be used to support the activator and/or catalyst systems of the invention are described in U.S. Pat. Nos. 4,701,432, 4,808,561, 4,912,075, 4,925,821, 4,937,217, 5,008,228, 5,238,892, 5,240,894, 5,332,706, 5,346,925, 5,422,325, 5,466,649, 5,466,766, 5,468,702, 5,529,965, 5,554,704, 5,629,253, 5,639,835, 5,625,015, 5,643,847, 5,665,665, 5,698,487, 5,714,424, 5,723,400, 5,723,402, 5,731,261, 5,759,940, 5,767,032, 5,770,664, 5,846,895 and 5,939,348 and U.S. application Ser. Nos. 271,598 filed Jul. 7, 1994 and 788,736 filed Jan. 23, 1997 and PCT publications WO 95/32995, WO 95/14044, WO 96/06187 and WO 97/02297, and EP-B1-0 685 494 all of which are herein fully incorporated by reference.

In another embodiment, an antistatic agent or surface modifier, that is used in the preparation of the supported catalyst system as described in PCT publication WO 96/11960, which is herein fully incorporated by reference, may be used with catalyst systems including the activator compounds of the invention. The catalyst systems of the invention may also be prepared in the presence of an olefin, for example hexene-1.

In another embodiment, activator and/or catalyst system of the invention may be combined with a carboxylic acid salt of a metal ester, for example aluminum carboxylates such as aluminum mono, di- and tri-stearates, aluminum octoates, oleates and cyclohexylbutyrates, as described in U.S. Pat. Nos. 6,300,436 and 6,306,984 incorporated herein by reference.

In another embodiment there is a method for producing a supported bulky ligand metallocene catalyst system, which maybe used to support the activator of the invention which is described below, and is described in U.S. application Ser. Nos. 265,533, filed Jun. 24, 1994 and 265,532, filed Jun. 24, 1994 and PCT publications WO 96/00245 and WO 96/00243 both published Jan. 4, 1996, all of which are herein fully incorporated by reference. In this method, the catalyst compound is slurried in a liquid to form a catalyst solution or emulsion. A separate solution is formed containing the activator. The liquid may be any compatible solvent or other liquid capable of forming a solution or the like with the catalyst compounds and/or activator. In the most preferred embodiment the liquid is a cyclic aliphatic or aromatic hydrocarbon, most preferably toluene. The catalyst compound and activator solutions are mixed together heated and added to a heated porous support or a heated porous support is added to the solutions such that the total volume of the bulky ligand metallocene-type catalyst compound solution and the activator solution or the bulky ligand metallocene-type catalyst compound and activator solution is less than four times the pore volume of the porous support, more preferably less than three times, even more preferably less than two times; preferred ranges being from 1.1 times to 3.5 times range and most preferably in the 1.2 to 3 times range.

In one embodiment, a method of forming a supported catalyst system, the amount of liquid, in which the activator of the invention and/or a catalyst compound is present, is in an amount that is less than four times the pore volume of the support material, more preferably less than three times, even more preferably less than two times; preferred ranges being from 1.1 times to 3.5 times range and most preferably in the 1.2 to 3 times range. In an alternative embodiment, the amount of liquid in which the activator is present is from one to less than one times the pore volume of the support material utilized in forming the supported activator.

Procedures for measuring the total pore volume of a porous support are well known in the art. Details of one of these procedures is discussed in Volume 1, *Experimental Methods in Catalytic Research* (Academic Press, 1968) (specifically see pages 67–96). This preferred procedure involves the use of a classical BET apparatus for nitrogen absorption. Another method well known in the art is described in Innes, *Total Porosity and Particle Density of Fluid Catalysts By Liquid Titration*, Vol. 28, No. 3, Analytical Chemistry 332–334 (March, 1956).

Polymerization Process

The activators of the invention, catalyst systems and supported catalyst systems utilizing the activators described above are suitable for use in any prepolymerization and/or polymerization process over a wide range of temperatures and pressures. The temperatures may be in the range of from −60° C. to about 280° C., preferably from 50° C. to about 200° C. In another embodiment the polymerization temperature is above 0° C., above 50° C., above 80° C., above 100° C., above 150° C., or above 200° C. In one embodiment the pressures employed may be in the range from 1 atmosphere to about 500 atmospheres or higher.

Polymerization processes include solution, gas phase, slurry phase and a high pressure process or a combination thereof. Particularly preferred is a gas phase or slurry phase polymerization of one or more olefin(s) at least one of which is ethylene or propylene.

In one embodiment, the process of the invention is directed toward a solution, high pressure, slurry or gas phase polymerization process of one or more olefin monomers having from 2 to 30 carbon atoms, preferably 2 to 12 carbon atoms, and more preferably 2 to 8 carbon atoms. The invention is particularly well suited to the polymerization of two or more olefin monomers of ethylene, propylene, butene-1, pentene-1,4-methyl-pentene-1, hexene-1, octene-1 and decene-1.

Other monomers useful in the process of the invention include ethylenically unsaturated monomers, diolefins having 4 to 18 carbon atoms, conjugated or nonconjugated dienes, polyenes, vinyl monomers and cyclic olefins. Non-limiting monomers useful in the invention may include norbornene, norbornadiene, isobutylene, isoprene, vinylbenzocyclobutane, styrenes, alkyl substituted styrene, ethylidene norbornene, dicyclopentadiene and cyclopentene.

In another embodiment of the process of the invention, a copolymer of ethylene is produced, where with ethylene, a comonomer having at least one alpha-olefin having from 4 to 15 carbon atoms, preferably from 4 to 12 carbon atoms, and most preferably from 4 to 8 carbon atoms, is polymerized in a gas phase process.

In another embodiment of the process of the invention, ethylene or propylene is polymerized with at least two different comonomers, optionally one of which may be a diene, to form a terpolymer.

In one embodiment, the invention is directed to a polymerization process, particularly a gas phase or slurry phase process, for polymerizing propylene alone or with one or more other monomers including ethylene, and/or other olefins having from 4 to 12 carbon atoms.

Typically in a gas phase polymerization process a continuous cycle is employed where in one part of the cycle of a reactor system, a cycling gas stream, otherwise known as a recycle stream or fluidizing medium, is heated in the reactor by the heat of polymerization. This heat is removed from the recycle composition in another part of the cycle by a cooling system external to the reactor. Generally, in a gas fluidized bed process for producing polymers, a gaseous stream containing one or more monomers is continuously cycled through a fluidized bed in the presence of a catalyst under reactive conditions. The gaseous stream is withdrawn from the fluidized bed and recycled back into the reactor. Simultaneously, polymer product is withdrawn from the reactor and fresh monomer is added to replace the polymerized monomer. (See for example U.S. Pat. Nos. 4,543,399, 4,588,790, 5,028,670, 5,317,036, 5,352,749, 5,405,922, 5,436,304, 5,453,471, 5,462,999, 5,616,661 and 5,668,228, all of which are fully incorporated herein by reference.)

The reactor pressure in a gas phase process may vary from about 100 psig (690 kPa) to about 500 psig (3448 kPa), preferably in the range of from about 200 psig (1379 kPa) to about 400 psig (2759 kPa), more preferably in the range of from about 250 psig (1724 kPa) to about 350 psig (2414 kPa).

The reactor temperature in a gas phase process may vary from about 30° C. to about 120° C., preferably from about 60° C. to about 115° C., more preferably in the range of from about 70° C. to about 110° C., and most preferably in the range of from about 70° C. to about 95° C. In another embodiment, the reactor temperature in a gas phase process is above 60° C.

Other gas phase processes contemplated by the process of the invention include series or multistage polymerization processes. Also gas phase processes contemplated by the invention include those described in U.S. Pat. Nos. 5,627,242, 5,665,818 and 5,677,375, and European publications EP-A-0 794 200 EP-B1-0 649 992, EP-A-0 802 202 and EP-B-634 421 all of which are herein fully incorporated by reference.

In another embodiment, the reactor utilized in the present invention is capable and the process of the invention is producing greater than 500 lbs of polymer per hour (227 Kg/hr) to about 200,000 lbs/hr (90,900 Kg/hr) or higher of polymer, preferably greater than 1000 lbs/hr (455 Kg/hr), more preferably greater than 10,000 lbs/hr (4540 Kg/hr), even more preferably greater than 25,000 lbs/hr (11,300 Kg/hr), still more preferably greater than 35,000 lbs/hr (15,900 Kg/hr), still even more preferably greater than 50,000 lbs/hr (22,700 Kg/hr) and most preferably greater than 65,000 lbs/hr (29,000 Kg/hr) to greater than 100,000 lbs/hr (45,500 Kg/hr).

A slurry polymerization process generally uses pressures in the range of from about 1 to about 50 atmospheres and even greater and temperatures in the range of 0° C. to about 120° C. In another embodiment, the slurry process temperature is above 100° C. In a slurry polymerization, a suspension of solid, particulate polymer is formed in a liquid polymerization diluent medium to which ethylene and comonomers and often hydrogen along with catalyst are added. The suspension including diluent is intermittently or continuously removed from the reactor where the volatile components are separated from the polymer and recycled, optionally after a distillation, to the reactor. The liquid diluent employed in the polymerization medium is typically an alkane having from 3 to 7 carbon atoms, preferably a branched alkane. The medium employed should be liquid under the conditions of polymerization and relatively inert. When a propane medium is used the process must be operated above the reaction diluent critical temperature and pressure. Preferably, a hexane or an isobutane medium is employed.

In another embodiment, the polymerization technique of the invention is referred to as a particle form polymerization, or a slurry process where the temperature is kept below the temperature at which the polymer goes into solution. Such technique is well known in the art, and described in for instance U.S. Pat. No. 3,248,179 which is fully incorporated herein by reference. Other slurry processes include those employing a loop reactor and those utilizing a plurality of stirred reactors in series, parallel, or combinations thereof. Non-limiting examples of slurry processes include continuous loop or stirred tank processes. Also, other examples of slurry processes are described in U.S. Pat. No. 4,613,484, which is herein fully incorporated by reference.

In another embodiment the reactor used in the slurry process of the invention is capable of and the process of the invention is producing greater than 2000 lbs of polymer per hour (907 Kg/hr), more preferably greater than 5000 lbs/hr (2268 Kg/hr), and most preferably greater than 10,000 lbs/hr (4540 Kg/hr). In another embodiment the slurry reactor used in the process of the invention is producing greater than 15,000 lbs of polymer per hour (6804 Kg/hr), preferably greater than 25,000 lbs/hr (11,340 Kg/hr) to about 100,000 lbs/hr (45,500 Kg/hr).

Examples of solution processes are described in U.S. Pat. Nos. 4,271,060, 5,001,205, 5,236,998 and 5,589,555 and PCT WO 99/32525, which are fully incorporated herein by reference.

In one embodiment of the process of the invention is the process, preferably a slurry or gas phase process is operated in the presence of the catalyst system of the invention and in the absence of or essentially free of any scavengers, such as triethylaluminum, trimethylaluminum, tri-isobutylaluminum and tri-n-hexylaluminum and diethyl aluminum chloride, dibutyl zinc and the like. This process is described in PCT publication WO 96/08520 and U.S. Pat. Nos. 5,712,352 and 5,763,543, which are herein fully incorporated by reference.

In another embodiment, the method of the invention provides for injecting the catalyst system of the invention into a reactor, particularly a gas phase reactor. In one embodiment the catalyst system is used in the unsupported form, preferably in a liquid form such as described in U.S. Pat. Nos. 5,317,036 and 5,693,727 and European publication EP-A-0 593 083, all of which are herein incorporated by reference. The polymerization catalyst in liquid form can be fed with an activator, and/or a support, and/or a supported activator together or separately to a reactor. The injection methods described in PCT publication WO 97/46599, which is fully incorporated herein by reference, may be utilized. Where an unsupported catalyst system is used the mole ratio of the metal of the Lewis acid activator component to the metal of the phenoxide transition metal catalyst compound is in the range of between 0.3:1 to 10,000:1, preferably 100:1 to 5000:1, and most preferably 500:1 to 2000:1.

Polymer Products

The polymers produced by the process of the invention can be used in a wide variety of products and end-use applications. The polymers produced by the process of the invention include linear low density polyethylene, elastomers, plastomers, high density polyethylenes, medium density polyethylenes, low density polyethylenes, polypropylene and polypropylene copolymers.

The polymers, typically ethylene based polymers, have a density in the range of from 0.86 g/cc to 0.97 g/cc, preferably in the range of from 0.88 g/cc to 0.965 g/cc, more preferably in the range of from 0.900 g/cc to 0.96 g/cc, even more preferably in the range of from 0.905 g/cc to 0.95 g/cc, yet even more preferably in the range from 0.910 g/cc to 0.940 g/cc, and most preferably greater than 0.915 g/cc, preferably greater than 0.920 g/cc, and most preferably greater than 0.925 g/cc. Density is measured in accordance with ASTM-D-1238.

The polymers produced by the process of the invention typically have a molecular weight distribution, a weight average molecular weight to number average molecular weight ($M_w/M_n$) of greater than 1.5 to about 15, particularly greater than 2 to about 10, more preferably greater than about 2.2 to less than about 8, and most preferably from 2.5 to 8.

Also, the polymers of the invention typically have a narrow composition distribution as measured by Composition Distribution Breadth Index (CDBI). Further details of determining the CDBI of a copolymer are known to those skilled in the art. See, for example, PCT Patent Application WO 93/03093, published Feb. 18, 1993, which is fully incorporated herein by reference. The polymers of the invention in one embodiment have CDBI's generally in the range of greater than 50% to 100%, preferably 99%, preferably in the range of 55% to 85%, and more preferably 60% to 80%, even more preferably greater than 60%, still even more preferably greater than 65%.

In another embodiment, polymers produced using a catalyst system of the invention have a CDBI less than 50%, more preferably less than 40%, and most preferably less than 30%.

The polymers of the present invention in one embodiment have a melt index (MI) or ($I_2$) as measured by ASTM-D-1238-E in the range from no measurable flow to 1000 dg/min, more preferably from about 0.01 dg/min to about 100 dg/min, even more preferably from about 0.1 dg/min to about 50 dg/min, and most preferably from about 0.1 dg/min to about 10 dg/min.

The polymers of the invention in an embodiment have a melt index ratio ($I_{21}/I_2$) ($I_{21}$ is measured by ASTM-D-1238-F) of from 10 to less than 25, more preferably from about 15 to less than 25.

The polymers of the invention in a preferred embodiment have a melt index ratio ($I_{21}/I_2$) ($I_{21}$ is measured by ASTM-D-1238-F) of from preferably greater than 25, more preferably greater than 30, even more preferably greater that 40, still even more preferably greater than 50 and most preferably greater than 65. In an embodiment, the polymer of the invention may have a narrow molecular weight distribution and a broad composition distribution or vice-versa, and may be those polymers described in U.S. Pat. No. 5,798,427 incorporated herein by reference.

In yet another embodiment, propylene based polymers are produced in the process of the invention. These polymers include atactic polypropylene, isotactic polypropylene, hemi-isotactic and syndiotactic polypropylene. Other propylene polymers include propylene block or impact copolymers. Propylene polymers of these types are well known in the art see for example U.S. Pat. Nos. 4,794,096, 3,248,455, 4,376,851, 5,036,034 and 5,459,117, all of which are herein incorporated by reference.

The polymers of the invention may be blended and/or coextruded with any other polymer. Non-limiting examples of other polymers include linear low density polyethylenes, elastomers, plastomers, high pressure low density polyethylene, high density polyethylenes, polypropylenes and the like.

Polymers produced by the process of the invention and blends thereof are useful in such forming operations as film, sheet, and fiber extrusion and co-extrusion as well as blow molding, injection molding and rotary molding. Films include blown or cast films formed by coextrusion or by lamination useful as shrink film, cling film, stretch film, sealing films, oriented films, snack packaging, heavy duty bags, grocery sacks, baked and frozen food packaging, medical packaging, industrial liners, membranes, etc. in food-contact and non-food contact applications. Fibers include melt spinning, solution spinning and melt blown fiber operations for use in woven or non-woven form to make filters, diaper fabrics, medical garments, geotextiles, etc. Extruded articles include medical tubing, wire and cable coatings, pipe, geomembranes, and pond liners. Molded articles include single and multi-layered constructions in the form of bottles, tanks, large hollow articles, rigid food containers and toys, etc.

EXAMPLES

In order to provide a better understanding of the present invention including representative advantages thereof, the following examples are offered.

4,5,6,7-Tetrafluoroindole was purchased from Oakwood Chemicals and used as received. Anhydrous toluene, dichloromethane, pentane, N,N-dimethylaniline, $AlCl_3$, 2.5 M n-butyl lithium in hexanes, & 1.0 M HCl in diethyl ether were purchased from Aldrich. $(1,3\text{-MeBuCp})_2ZrCl_2$, was purchased from Boulder Chemical Co. $(1,3\text{-MeBuCp})_2ZrMe_2$, $(nPrCp)_2HfMe_2$, $(CH_2)_3Si(CpMe_4)(Ind)ZrMe_2$, $(CH_2)_4Si(CpMe_4)$ $(Cp)ZrMe_2$, were obtained via the methylation of the corresponding metallocene dichlorides with two equivalents of a 1.4 M methyl lithium solution in diethyl ether. rac-$Me_2Si(H_4Ind)_2ZrMe_2$ was purchased from Witco. rac-$Me_2Si(4\text{-Ph-2-MeInd})_2ZrMe_2$ was obtained via a procedure analogous to the synthesis published in U.S. Pat. No. 5,770,753. (CpMe4)2HfMe2, rac-Me2Si(2-MeInd)2ZrMe2, $(p\text{-}Et_3SiPh)_2C(2,7\text{-}t\text{-}Bu_2Fl)(Cp)HfMe_2$, (nPrCp)2HfCl2 was synthesized.

Example 1

Preparation of $[(C_6H_5)(CH_3)_2NH][Al(NC_8F_4)_4]_2$ 9.8 grams of 4,5,6,7-tetrafluoroindole was added to 300 mls of diethyl ether in a one liter Schlenk flask. The flask was equipped with a addition funnel loaded with 19.4 mls of 2.67 M n-butyl lithium in hexane. The solution was cooled to −35° C. and n-butyl lithium was added slowly over the course of one half hour. 1.73 grams of $AlCl_3$ was added as a solid to the solution. After several hours the solution was allowed to warm to room temperature. The solvent was concentrated, filtered through celite, and removed. Several pentane washes yielded the lithium etherate salt. One equivalent of $(CH_3)_2(C_6H_5)NHCl$ (2.00 grams) was added in a solution of dichoromethane. The resulting slurry stirred overnight. The slurry was filtered through celite, and the solution was concentrated under vacuum. The product crystallized from the concentrated dichloromethane solution at −35° C. $^{19}F$ NMR ($CD_2Cl_2$) δ −152.4 (m, 4F), −156.3 (m, 4F), −171.1 (m, 4F), −173.1 (m, 4F). $^1H$ NMR ($CD_2Cl_2$): δ 3.39(s, 6H), 6.62, (t, 4H), 7.16 (s, 1H), 7.21 (m, 4H), 7.29 (m, 2H), 7.57 (m, 3H).

Example 2

Ethylene-α-Olefin Co-Polymerizations

Polymerizations, utilizing the activator in Example 1, were performed in a glass-lined 20-mililiter autoclave reactor equipped with a mechanical stirrer, an external heater for temperature control, a septum inlet and a regulated supply of dry nitrogen and ethylene in an inert atmosphere (Nitrogen) glove box. The reactor was dried and degassed thoroughly at 115° C. The diluent, comonomer, and scavenger (if used), were added at room temperature and atmospheric pressure. The reactor was then brought to process pressure and charged with ethylene while stirring at 800 RPM. The activator and catalyst were added via syringe with the reactor at process conditions. The polymerization was continued while maintaining the reaction vessel within 3° C. of the target process temperature and 5 psig of target process pressure (by automatic addition of ethylene on demand) until a fixed uptake of ethylene was noted (corresponding to ca. 0.15 g polymer) or until a maximum reaction time of 20 minutes had passed. The reaction was stopped by pressurizing the reactor to 30 psig above the target process pressure with a gas mixture composed of 5 mol % Oxygen in Argon. The polymer was recovered by vacuum centrifugation of the reaction mixture. Bulk polymerization activity was calculated by dividing the yield of polymer by the total weight of the catalyst charge by the time in hours and by the absolute monomer pressure in atmospheres. The specific polymerization activity was calculated by dividing the yield of polymer by the total number of millimoles of transition metal contained in the catalyst charge by the time in hours and by the absolute monomer pressure in atmospheres. Pertinent data is summarized in Table 1.

Example 3

Potassium tetrafluoroindolyl 8.65 grams of 4,5,6,7-tetrafluoroindole were added to 200 mls of tetrahydofuran in a 500 ml flask. The solution was cooled to −35° C. 1.83 grams of potassium hydride were added as a solid in small portions over a twenty-minute period. The evolution of hydrogen gas was observed. The reaction was allowed to warm to room temperature. 400 mls of pentane was added to precipitate the product. The resulting white powder was filtered and dried under vacuum. (97% yield). $^{19}F$ NMR (THF-d8) δ −157.4 (m, 1F), −169.6 (m, 1F), −184.5 (m, 1F), −184.9 (m, 1F). $^1H$ NMR (THF-d8): δ 6.32(m, 1H), 7.32, (d, 1H).

Example 4

3-triphenylmethyl-4,5,6,7-tetrafluoroindole

Potassium tetrafluoroindolyl and one equivalent of trityl chloride were combined in tetrahydrofuran. The solvent was removed after several hours. The addition of pentane yielded a white slurry. The slurry was filtered and the pentane solution was concentrated from which the product was obtained. $^{19}F$ NMR (C6D6) δ −157.4 (m, 1F), −169.6 (m, 1F), −184.5 (m, 1F), −184.9 (m, 1F). $^1H$ NMR (C6D6): δ 6.29 (d, 1H), 6.74(s (br), 1H), 7.15, (m, 9H), 7.40 (d, 6H).

Example 5

Potassium(tetrahydrofuran)n 3-triphenylmethyl-4,5,6,7-tetrafluoroindolyl 2.0 grams of 3-triphenylmethyl-4,5,6,7-tetrafluoroindole was added to 200 mls of tetrahydofuran in a 100 ml flask. The solution was cooled to −35° C. 0.186 grams of potassium hydride were added as a solid in small portions over a twenty-minute period. The evolution of hydrogen gas was observed. The reaction was allowed to warm to room temperature yielding a golden solution. After solvent removal via vacuum, pentane addition resulted in a slurry of the product. The resulting tan-white powder was filtered and dried under vacuum. $^{19}F$ NMR (THF-d8) δ −149.1 (m, 1F), −170.9 (m, 1F), −183.5 (m, 1F), −184.7 (m, 1F). $^1H$ NMR (THF-d8) δ 1.80 (m), 3.62 (m), 6.75 (s, 1H) 7.06 (m, 9H), 7.20 (d, 6H).

Example 6

K[Al(3-triphenylmethyl-4,5,6,7-tetrafluoroindolyl)4]

Potassium(tetrahydrofuran)n 3-triphenylmethyl-4,5,6,7-tetrafluoroindolyl (2.25 grams) were combined with 0.0986 grams of aluminum trichloride in diethyl ether. A white slurry results. The slurry was allowed to stir overnight. The KCl solids were filtered off and the solution was dried under vacuum. Dichloromethane was added to slurry the product and subsequently removed under vacuum. This step was repeated several times to remove residual diethyl ether and tetrahydrofuran. $^{19}$F NMR (THF-d8) δ −146.1 (m, 4F), −159.7 (m, 4F), −173.3 (m, 4F), −176.8 (m, 4F). $^1$H NMR (THF-d8) δ 6.60 (s, 4H) 7.09 (m, 60H).

Example 7

[(C$_6$H$_5$)(CH$_3$)$_2$NH[]Al(3-triphenylmethyl-4,5,6,7-tetrafluoroindolyl)4] (Referred to as Activator A in Table 2B)

K[Al(3-triphenylmethyl-4,5,6,7-tetrafluoroindolyl)4] (0.46 grams) and one equivalent of (CH$_3$)$_2$(C$_6$H$_5$)NHCl (0.0387 grams) was added in a solution of dichloromethane. The resulting slurry stirred overnight. The slurry was filtered through celite, and the solution was concentrated under vacuum. The product crystallized from the concentrated dichloromethane solution at −35° C. $^{19}$F NMR (CD$_2$Cl$_2$) δ −144.9 (m, 4F), −157.2 (m, 4F), −170.6 (m, 4F), −174.1 (m, 4F). $^1$H NMR (CD$_2$Cl$_2$): δ 3.25 (s, 6H), 6.55, (s, 4H), 7.08 (s, (br) 60H), 7.3 (m, 3H), 7.55 (m, 2H). Polymerizations were conducted in accordance with Example 2. Pertinent data is summarized in Table 2B.

Example 8

3-(4,4',4"-Trifluorotrityl)-4,5,6,7-tetrafluoroindole (TTFI)

In a 250 ml round bottom flask, potassium tetrafluoroindolyl (5.02, 22.1 mmol) was dissolved into 125 ml of THF. To this stirring solution, 4,4',4"-trifluorotrityl bromide was added at room temperature. There was an immediate color change from yellow to a deep purple. After several hours the mixture yielded a golden slurry. The solvent was removed in vacuo and pentane added. The slurry was filtered through a frit to remove KBr. The pentane solution was dried yielding 11.5 grams (94% yield) of 3-(4,4',4"-Trifluorotrityl)-4,5,6,7-tetrafluoroindole. $^1$H NMR (CD$_2$Cl$_2$): δ 8.67 (NH, s), 7.23–6.92 (12 H, m), 6.77 (CH, d), 3.72 (2H, m), 1.83 (2H, m); $^{19}$F NMR(CD$_2$Cl$_2$): δ −117.6 (m 3F, −141.9 (m, 1F), −163.2 (m, 1F), −166.2 (m, 1F), −170.4 (m, 1F). NOTE: Minor product(s) as detected by $^{19}$F NMR(CD$_2$Cl$_2$): −115.1, −116.4, −146.4, −151.3, −151.8, −162.4, −167.7, −171.2.

Example 9

K(THF)[TTFI]

In a 250 ml round bottom flask, 3-(4,4',4"-Trifluorotrityl)-4,5,6,7-tetrafluoroindole (TTFI), (8.74 grams, 16.8 mmol) was dissolved in 100 ml of THF. The flask was then cooled to −35° C. and stirred. Potassium hydride (0.672 grams, 16.8 mmol) was added slowly via spatula. Hydrogen gas was observed bubbling out of the mixture. The mixture was allowed to stir at −35° C. for another 20 minutes then brought up to room temperature. The THF was removed by vacuum to yield a purple crystalline solid (10.0 grams, 92% yield). $^1$H NMR (THF-d8): δ 7.20 (6H, m), 6.85 (6H, m), 6.73 (H, s), 3.63 (4H, m), 1.77 (4H, m). $^{19}$F NMR: δ −122.0 (3F), −150.0 (F), −169.9 (F), −182.5 (F), −183.8 (F). NOTE: Minor product(s) carried over from previous synthesis: $^{19}$F NMR(CD$_2$Cl$_2$): □ −117.4, −117.5, −119.7, −143.8, −148.0, −154.6, −157.1, −168.2, −168.8, −169.4, −171.3, −172.0, −182.8.

Example 10

K(TTFI)$_4$Al

In a 250 ml round bottom flask, [TTFI]K(THF) (10.3 grams, 15.4 mmol) was slurried in 150 ml of CH$_2$Cl$_2$. Aluminum chloride (0.513 grams, 3.8 mmol) was added and the mixture was stirred for several hours. The contents were then filtered through Celite and the resulting filtrate was reduced to 25 mls. Pentane was added and the solids collected and dried under vacuum to yield 1.90 grams (25% yield) of product. $^1$H NMR (THF-d8): δ 7.13 (24H, m) 6.90 (24H, m), 6.53 (4H, s). $^{19}$F NMR: δ −120.6 (m, 12F), −145.7 (m, 4F), −160.1 (m, 4F), −172.6 (m, 4F), −175.2(m, 4F).

Example 11

[(C$_6$H$_5$)(CH$_3$)$_2$NH][Al(3-4,4',4"-trifluorotrityl-4,5,6,7-tetrafluoroindolyl)$_4$] (Referred to as Activator B in Table 2B)

In a 250 ml round bottom flask, (TTFI)$_4$AlK (1.90 grams, 0.9 mmol) was slurried in 100 ml of CH$_2$Cl$_2$. Dimethylanilinium chloride (0.149 grams, 0.9 mmol) was added to the stirring solution at room temperature. The mixture was stirred for two hours and then filtered through Celite. The CH$_2$Cl$_2$ was reduced and pentane added. The resulting solid was filtered, washed with pentane and dried under vacuum to yield 1.20 grams (61%) of product. $^1$H NMR (CD$_2$Cl$_2$): δ 7.72 (H, m) 7.63 (2H, m), 7.30 (2H, m), 7.05 (24H, m), 6.85 (24H, m), 6.58 (H, t) 6.48 (4H, d), 3.41 (6H, m). 19F NMR: δ −118.4 (m, 12F), −144.3 (m, 4F), −157.5 (m, 4F), −170.1 (m, 4F), −172.9 (m, 4F). Polymerizations were conducted in accordance with Example 2. Pertinent data is summarized in Tables 2A and 2B.

TABLE 1

Polymerization Data Utilizing [(C$_6$H$_5$)(CH$_3$)$_2$NH][Al(NC$_8$F$_4$)$_4$]$_2$

| Catalyst | | Average Mw | Average Mn | Average PDI | Comonomer Incorporation | Yield | Activity (g/mmol*hr) |
|---|---|---|---|---|---|---|---|
| (1,3-MeBuCp)2ZrMe2 | | 188383 | 79347 | 2.4 | 0.8 | 0.1093 | 332.1 |
| (1,3-MeBuCp)2ZrMe2 | | 92742 | 31516 | 2.9 | 4.5 | 0.1222 | 171.5 |
| (1,3-MeBuCp)2ZrMe2 | | 76597 | 27101 | 2.8 | 4.3 | 0.1104 | 202.3 |
| | average | 119241 | 45988 | 2.7 | 3.2 | 0.1140 | 235.3 |
| | stddev | 60421 | 28974 | 0.3 | 2.1 | 0.0072 | 85.2 |
| (CpMe4)2HfMe2 | | 156106 | 79586 | 2.0 | 5.6 | 0.1047 | 68.1 |
| (CpMe4)2HfMe2 | | 149961 | 74672 | 2.0 | 4.9 | 0.1039 | 70.4 |

TABLE 1-continued

Polymerization Data Utilizing
[(C$_6$H$_5$)(CH$_3$)$_2$NH][Al(NC$_8$F$_4$)$_4$]$_2$

| Catalyst | | Average Mw | Average Mn | Average PDI | Comonomer Incorporation | Yield | Activity (g/mmol*hr) |
|---|---|---|---|---|---|---|---|
| (CpMe4)2HfMe2 | | 159838 | 65776 | 2.4 | 3.8 | 0.1016 | 69.1 |
| | average | 155302 | 73345 | 2.1 | 4.8 | 0.1034 | 69.2 |
| | stddev | 4987 | 7000 | 0.2 | 0.9 | 0.0016 | 1.2 |
| p-t-BuPh2Si(Fl)(Cp)HfMe2 | | 781094 | 330162 | 2.4 | 21.1 | 0.1062 | 21.3 |
| p-t-BuPh2Si(Fl)(Cp)HtMe2 | | 459552 | 177429 | 2.6 | 23.3 | 0.1601 | 45.3 |
| p-t-BuPh2Si(Fl)(Cp)HfMe2 | | 457276 | 173432 | 2.6 | 21.0 | 0.1677 | 45.2 |
| | average | 565974 | 227007 | 2.5 | 21.8 | 0.1447 | 37.3 |
| | stddev | 186303 | 89357 | 0.1 | 1.3 | 0.0335 | 13.8 |
| rac-Me2Si(2-Me-4-PhInd)2ZrMe2 | | 186375 | 77767 | 2.4 | 25.9 | 0.1937 | 252.7 |
| rac-Me2Si(2-Me-4-PhInd)2ZrMe2 | | 159308 | 55205 | 2.9 | 26.9 | 0.2015 | 262.8 |
| rac-Me2Si(2-Me-4-PhInd)2ZrMe2 | | 174760 | 57112 | 3.1 | 26.5 | 0.2078 | 237.5 |
| | average | 173481 | 63361 | 2.8 | 26.4 | 0.2010 | 251.0 |
| | stddev | 13579 | 12512 | 0.4 | 0.5 | 0.0071 | 12.8 |
| Si—(CH2)4(CpMe4)(Cp)ZrMe2 | | 139229 | 78011 | 1.8 | 3.1 | 0.0178 | 16.3 |
| Si—(CH2)4(CpMe4)(Cp)ZrMe2 | | | | | | 0.0092 | 0.1 |
| Si—(CH2)4(CpMe4)(Cp)ZrMe2 | | 132629 | 71307 | 1.9 | 2.7 | 0.0246 | 0.2 |
| | average | 135929 | 74659 | 1.9 | 2.9 | 0.0172 | 5.5 |
| | stddev | 4667 | 4741 | 0.1 | 0.3 | 0.0077 | 9.3 |
| Me2Si(CpMe4)(Fl)ZrMe2 | | 268049 | 172954 | 1.5 | 3.3 | 0.0965 | 80.4 |
| Me2Si(CpMe4)(Fl)ZrMe2 | | 291289 | 187621 | 1.6 | 3.5 | 0.0995 | 75.8 |
| Me2Si(CpMe4)(Fl)ZrMe2 | | 289832 | 179786 | 1.6 | 3.8 | 0.1018 | 80.9 |
| | average | 283057 | 180120 | 1.6 | 3.5 | 0.0993 | 79.0 |
| | stddev | 13017 | 7339 | 0.1 | 0.3 | 0.0027 | 2.8 |
| Si—(CH2)3(CpMe4)(Ind)ZrMe2 | | 58375 | 37747 | 1.5 | 6.4 | 0.0607 | 12.4 |
| Si—(CH2)3(CpMe4)(Ind)ZrMe2 | | 55104 | 35297 | 1.6 | 5.6 | 0.0962 | 103.5 |
| Si—(CH2)3(CpMe4)(Ind)ZrMe2 | | 56719 | 36781 | 1.5 | 5.9 | 0.0903 | 55.1 |
| | average | 56733 | 36608 | 1.5 | 6.0 | 0.0824 | 57.0 |
| | stddev | 1635 | 1234 | 0.1 | 0.4 | 0.0190 | 45.6 |
| (nPrCp)2HfMe2 | | | | | | 0.0090 | 0.1 |
| (nPrCp)2HfMe2 | | 275454 | 78742 | 3.5 | 4.4 | 0.0811 | 55.1 |
| (nPrCp)2HfMe2 | | 301777 | 92702 | 3.3 | 4.0 | 0.0862 | 54.4 |
| | average | 288615 | 85722 | 3.4 | 4.2 | 0.0588 | 36.6 |
| | stddev | 18613 | 9871 | 0.1 | 0.3 | 0.0432 | 31.6 |
| rac-Me2Si(2-MeInd)ZrMe2 | | 118377 | 67957 | 1.7 | 7.2 | 0.1303 | 217.2 |
| rac-Me2Si(2-MeInd)ZrMe2 | | 109596 | 60845 | 1.8 | 9.5 | 0.1359 | 207.7 |
| rac-Me2Si(2-MeInd)ZrMe2 | | 111984 | 63544 | 1.8 | 10.5 | 0.1339 | 204.7 |
| | average | 113319 | 64115 | 1.8 | 9.1 | 0.1334 | 209.9 |
| | stddev | 4540 | 3590 | 0.1 | 1.7 | 0.0028 | 6.5 |
| rac-Me2Si(2-Me-4-PhInd)2ZrMe2 | | 185773 | 100708 | 1.8 | 15.9 | 0.1367 | 166.5 |
| rac-Me2Si(2-Me-4-PhInd)2ZrMe2 | | 206017 | 130633 | 1.6 | 11.3 | 0.1051 | 60.1 |
| rac-Me2Si(2-Me-4-PhInd)2ZrMe2 | | 179135 | 98477 | 1.8 | 19.8 | 0.1455 | 127.0 |
| | average | 190309 | 109939 | 1.7 | 15.7 | 0.1291 | 117.9 |
| | stddev | 14003 | 17956 | 0.1 | 4.3 | 0.0212 | 53.8 |
| rac-Me2Si(H4-Ind)2ZrMe2 | | 257090 | 145393 | 1.8 | 3.8 | 0.0447 | 10.4 |
| rac-Me2Si(H4-Ind)2ZrMe2 | | 175850 | 90476 | 1.9 | 2.8 | 0.0713 | 56.9 |
| rac-Me2Si(H4-Ind)2ZrMe2 | | 199064 | 106541 | 1.9 | 3.7 | 0.0623 | 36.9 |
| | average | 210668 | 114136 | 1.9 | 3.4 | 0.0594 | 34.7 |
| | stddev | 41845 | 28236 | 0.1 | 0.6 | 0.0135 | 23.3 |
| Me2SilylMe4Cp(C12H23N)TiMe2 | | 306988 | 175956 | 1.7 | 29.8 | 0.1509 | 74.7 |
| Me2SilylMe4Cp(C12H23N)TiMe2 | | 273790 | 107909 | 2.5 | 28.2 | 0.1575 | 107.1 |
| Me2SilylMe4Cp(C12H23N)TiMe2 | | 335409 | 127871 | 2.6 | 26.8 | 0.1589 | 132.4 |
| | average | 305396 | 137245 | 2.3 | 28.3 | 0.1558 | 104.7 |
| | stddev | 30840 | 34978 | 0.5 | 1.5 | 0.0043 | 28.9 |
| {[(2,4,6-Me3C6H2)NCH2CH2]2NH}Hf(CH2Ph)2 | | 199201 | 98497 | 2 | 13.7 | 0.0977 | 42.6 |
| {[(2,4,6-Me3C6H2)NCH2CH2]2NH}Hf(CH2Ph)2 | | 192774 | 116087 | 1.7 | 13.1 | 0.0958 | 43.9 |
| {[(2,4,6-Me3C6H2)NCH2CH2]2NH}Hf(CH2Ph)2 | | 218916 | 136693 | 1.6 | 13.4 | 0.0991 | 50.1 |
| | average | 203630 | 117092 | 1.8 | 13.4 | 0.0975 | 45.5 |
| | stddev | 13622 | 19118 | 0.2 | 0.3 | 0.0017 | 4.0 |

TABLE 2A

Polymerization Data Utilizing
[(C₆H₅)(CH₃)₂NH][Al(3-4,4',4"-trifluorotrityl-4,5,6,7-tetrafluoroindolyl)₄]

| Catalyst | | Average Mw | Average Mn | Average PDI | Comonomer Incorporation | Yield | Activity (g/mmol*hr) |
|---|---|---|---|---|---|---|---|
| Si—(CH2)4(CpMe4)(Cp)ZrMe2 | | 68099 | 13799 | 4.9 | 12 | 0.204 | 184 |
| Si—(CH2)4(CpMe4)(Cp)ZrMe2 | | 0 | 0 | 0 | 0 | 0.203 | 206 |
| Si—(CH2)4(CpMe4)(Cp)ZrMe2 | | 59906 | 14879 | 4 | 9.4 | 0.201 | 204 |
| | average | 42668 | 9559 | 3 | 7.1 | 0.2 | 198.3 |
| | stddev | 37178 | 8296 | 2.6 | 6.3 | 0 | 12.4 |
| (1,3-MeBuCp)2ZrMe2 | | 88022 | 13830 | 6.4 | 4.7 | 0.156 | 179 |
| (1,3-MeBuCp)2ZrMe2 | | 91220 | 12966 | 7 | 4.9 | 0.161 | 184 |
| (1,3-MeBuCp)2ZrMe2 | | 93882 | 11473 | 8.2 | 5 | 0.17 | 155 |
| | average | 91041 | 12756 | 7.2 | 4.9 | 0.2 | 172.8 |
| | stddev | 2934 | 1192 | 0.9 | 0.2 | 0 | 15.5 |
| Si—(CH2)3(CpMe4)(Ind)ZrMe2 | | 42126 | 9344 | 4.5 | 23.1 | 0.211 | 325 |
| Si—(CH2)3(CpMe4)(Ind)ZrMe2 | | 41318 | 9741 | 4.2 | 23.2 | 0.218 | 393 |
| Si—(CH2)3(CpMe4)(Ind)ZrMe2 | | 48016 | 10653 | 4.5 | 22.3 | 0.214 | 375 |
| | average | 43820 | 9913 | 4.4 | 22.9 | 0.2 | 364.3 |
| | stddev | 3656 | 671 | 0.2 | 0.5 | 0 | 35.6 |
| rac-Me2Si(2-MeInd)ZrMe2 | | 128631 | 21079 | 6.1 | 19.8 | 0.206 | 152 |
| rac-Me2Si(2-MeInd)ZrMe2 | | 133307 | 20039 | 6.7 | 20.3 | 0.208 | 166 |
| rac-Me2Si(2-MeInd)ZrMe2 | | 119772 | 18778 | 6.4 | 20.5 | 0.202 | 165 |
| | average | 127237 | 19965 | 6.4 | 20.2 | 0.2 | 161 |
| | stddev | 6874 | 1152 | 0.3 | 0.4 | 0 | 7.7 |
| (CpMe4)2HfMe2 | | | | | | 0 | 0 |
| (CpMe4)2HfMe2 | | | | | | 0 | 0 |
| (CpMe4)2HfMe2 | | | | | | 0 | 0 |
| | average | | | | | 0 | 0 |
| | stddev | | | | | 0 | 0 |
| rac-Me2Si(2-Me-4-PhInd)2ZrMe2 | | 160409 | 21846 | 7.3 | 33.1 | 0.24 | 171 |
| rac-Me2Si(2-Me-4-PhInd)2ZrMe2 | | 151532 | 22379 | 6.8 | 37.7 | 0.245 | 153 |
| rac-Me2Si(2-Me-4-PhInd)2ZrMe2 | | 160061 | 25410 | 6.3 | 33.7 | 0.245 | 131 |
| | average | 157334 | 23212 | 6.8 | 34.8 | 0.2 | 151.4 |
| | stddev | 5028 | 1922 | 0.5 | 2.5 | 0 | 20.2 |
| rac-Me2Si(H4-Ind)2ZrMe2 | | 52165 | 7964 | 6.5 | 12.9 | 0.197 | 301 |
| rac-Me2Si(H4-Ind)2ZrMe2 | | 54924 | 7761 | 7.1 | 12.8 | 0.194 | 271 |
| rac-Me2Si(H4-Ind)2ZrMe2 | | 54013 | 7798 | 6.9 | 11.4 | 0.179 | 288 |
| | average | 53701 | 7841 | 6.8 | 12.4 | 0.2 | 286.7 |
| | stddev | 1406 | 108 | 0.3 | 0.8 | 0 | 15.3 |

TABLE 2B

Polymerization Data Utilizing: Activator B
[(C₆H₅)(CH₃)₂NH][Al(3-4,4',4"-trifluorotrityl-4,5,6,7-tetrafluoroindolyl)₄]
and Activator A [(C₆H₅)(CH₃)₂NH][Al(3-triphenylmethyl-4,5,6,7-tetrafluoroindolyl)4]

| Catalyst | Activator | | Average Mw | Average Mn | Average PDI | Comonomer Incorporation | Yield | Activity (g/mmol*hr) |
|---|---|---|---|---|---|---|---|---|
| Si—(CH2)4(CpMe4)(Cp)ZrMe2 | B | | | | | | 0 | 0 |
| Si—(CH2)4(CpMe4)(Cp)ZrMe2 | B | | | | | | 0.014 | 0.1 |
| Si—(CH2)4(CpMe4)(Cp)ZrMe2 | B | | | | | | 0.003 | 0 |
| | | average | | | | | 0 | 0.1 |
| | | stddev | | | | | 0 | 0.1 |
| Si—(CH2)4(CpMe4)(Cp)ZrMe2 | A | | | | | | 0 | 0 |
| Si—(CH2)4(CpMe4)(Cp)ZrMe2 | A | | | | | | 0 | 0 |
| Si—(CH2)4(CpMe4)(Cp)ZrMe2 | A | | | | | | 0 | 0 |
| | | average | | | | | 0 | 0 |
| | | stddev | | | | | 0 | 0 |
| (1,3-MeBuCp)2ZrMe2 | B | | | | | | 0.013 | 0.1 |
| (1,3-MeBuCp)2ZrMe2 | B | | 276381 | 105672 | 2.6 | 2.4 | 0.03 | 1.3 |
| (1,3-MeBuCp)2ZrMe2 | B | | 269216 | 85159 | 3.2 | 2.6 | 0.037 | 2.7 |
| | | average | 272799 | 95416 | 2.9 | 2.5 | 0 | 1.4 |
| | | stddev | 5066 | 14505 | 0.4 | 0.1 | 0 | 1.3 |
| (1,3-MeBuCp)2ZrMe2 | A | | | | | | 0.003 | 0 |
| (1,3-MeBuCp)2ZrMe2 | A | | | | | | 0.002 | 0 |
| (1,3-MeBuCp)2ZrMe2 | A | | | | | | 0.003 | 0 |
| | | average | | | | | 0 | 0 |
| | | stddev | | | | | 0 | 0 |
| Si—(CH2)3(CpMe4)(Ind)ZrMe2 | B | | 82460 | 42453 | 1.9 | 8.1 | 0.06 | 7.5 |
| Si—(CH2)3(CpMe4)(Ind)ZrMe2 | B | | 61201 | 28245 | 2.2 | 14.9 | 0.167 | 149 |
| Si—(CH2)3(CpMe4)(Ind)ZrMe2 | B | | 67787 | 32847 | 2.1 | 12.6 | 0.147 | 88 |
| | | average | 70483 | 34515 | 2.1 | 11.9 | 0.1 | 81.5 |
| | | stddev | 10883 | 7249 | 0.2 | 3.5 | 0.1 | 71 |

TABLE 2B-continued

Polymerization Data Utilizing: Activator B
[(C₆H₅)(CH₃)₂NH][Al(3-4,4',4''-trifluorotrityl-4,5,6,7-tetrafluoroindolyl)₄]
and Activator A [(C₆H₅)(CH₃)₂NH][Al(3-triphenylmethyl-4,5,6,7-tetrafluoroindolyl)4]

| Catalyst | Activator | | Average Mw | Average Mn | Average PDI | Comonomer Incorporation | Yield | Activity (g/mmol*hr) |
|---|---|---|---|---|---|---|---|---|
| Si—(CH2)3(CpMe4)(Ind)ZrMe2 | A | | 77513 | 42026 | 1.8 | 6.6 | 0.057 | 1.8 |
| Si—(CH2)3(CpMe4)(Ind)ZrMe2 | A | | 73647 | 39084 | 1.9 | 6.8 | 0.04 | 1.1 |
| Si—(CH2)3(CpMe4)(Ind)ZrMe2 | A | | 73845 | 37945 | 1.9 | 6.5 | 0.047 | 1.4 |
| | | average | 75002 | 39685 | 1.9 | 6.6 | 0 | 1.4 |
| | | stddev | 2177 | 2106 | 0.1 | 0.2 | 0 | 0.4 |
| rac-Me2Si(2-MeInd)ZrMe2 | B | | 151770 | 58079 | 2.6 | 13.8 | 0.168 | 112.3 |
| rac-Me2Si(2-MeInd)ZrMe2 | B | | 153782 | 58774 | 2.6 | 13.5 | 0.17 | 107.4 |
| rac-Me2Si(2-MeInd)ZrMe2 | B | | 184662 | 83682 | 2.2 | 6.9 | 0.112 | 27.7 |
| | | average | 163405 | 66845 | 2.5 | 11.4 | 0.2 | 82.5 |
| | | stddev | 18437 | 14585 | 0.2 | 3.9 | 0 | 47.5 |
| rac-Me2Si(2-MeInd)ZrMe2 | A | | 180463 | 80431 | 2.2 | 4 | 0.066 | 5.7 |
| rac-Me2Si(2-MeInd)ZrMe2 | A | | 182251 | 72126 | 2.5 | 6 | 0.065 | 5.8 |
| rac-Me2Si(2-MeInd)ZrMe2 | A | | 175279 | 63638 | 2.8 | 4.4 | 0.062 | 4.8 |
| | | average | 179331 | 72065 | 2.5 | 4.8 | 0.1 | 5.5 |
| | | stddev | 3621 | 8397 | 0.3 | 1.1 | 0 | 0.5 |
| (CpMe4)2HfMe2 | B | | 331350 | 76538 | 4.3 | 3.4 | 0.028 | 0.3 |
| (CpMe4)2HfMe2 | B | | | | | | 0.007 | 0.1 |
| (CpMe4)2HtMe2 | B | | 277194 | 41814 | 6.6 | 3 | 0.017 | 0.2 |
| | | average | 304272 | 59176 | 5.5 | 3.2 | 0 | 0.2 |
| | | stddev | 38294 | 24554 | 1.6 | 0.3 | 0 | 0.1 |
| (CpMe4)2HfMe2 | A | | | | | | 0.004 | 0 |
| (CpMe4)2HfMe2 | A | | | | | | 0.002 | 0 |
| (CpMe4)2HfMe2 | A | | | | | | 0.003 | 0 |
| | | average | | | | | 0 | 0 |
| | | stddev | | | | | 0 | 0 |
| rac-Me2Si(2-Me-4-PhInd)2ZrMe2 | B | | 238963 | 100194 | 2.4 | 21.7 | 0.157 | 36.6 |
| rac-Me2Si(2-Me-4-PhInd)2ZrMe2 | B | | 186041 | 56925 | 3.3 | 27.6 | 0.209 | 88.5 |
| rac-Me2Si(2-Me-4-PhInd)2ZrMe2 | B | | 206072 | 86081 | 2.4 | 23 | 0.171 | 51.4 |
| | | average | 210359 | 81067 | 2.7 | 24.1 | 0.2 | 58.8 |
| | | stddev | 26720 | 22066 | 0.5 | 3.1 | 0 | 26.7 |
| rac-Me2Si(2-Me-4-PhInd)2ZrMe2 | A | | 270216 | 121532 | 2.2 | 15.9 | 0.058 | 3.2 |
| rac-Me2Si(2-Me-4-PhInd)2ZrMe2 | A | | 239106 | 110175 | 2.2 | 16.1 | 0.06 | 3.1 |
| rac-Me2Si(2-Me-4-PhInd)2ZrMe2 | A | | 241889 | 99717 | 2.4 | 17.3 | 0.06 | 3.1 |
| | | average | 250404 | 110475 | 2.3 | 16.4 | 0.1 | 3.1 |
| | | stddev | 17214 | 10911 | 0.1 | 0.8 | 0 | 0 |
| rac-Me2Si(H4-Ind)2ZrMe2 | B | | | | | | 0.008 | 0.1 |
| rac-Me2Si(H4-Ind)2ZrMe2 | B | | | | | | 0.008 | 0.1 |
| rac-Me2Si(H4-Ind)2ZrMe2 | B | | | | | | 0.003 | 0 |
| | | average | | | | | 0 | 0.1 |
| | | stddev | | | | | 0 | 0 |
| rac-Me2Si(H4-Ind)2ZrMe2 | A | | | | | | 0 | 0 |
| rac-Me2Si(H4-Ind)2ZrMe2 | A | | 472855 | 28424 | 16.6 | 1.6 | 0.1 | 0.9 |
| rac-Me2Si(H4-Ind)2ZrMe2 | A | | 461960 | 28428 | 16.3 | 1.4 | 0.1 | 0.9 |
| | | average | 467408 | 28426 | 16.5 | 1.5 | 0.1 | 0.6 |
| | | stddev | 7704 | 3 | 0.2 | 0.1 | 0.1 | 0.5 |

What is claimed is:

1. A catalyst system comprising a catalyst compound and an activator compound wherein the activator compound is represented by the formula:

$Cat^+[M(JY)_x]^-$ wherein M is a Group 13 atom attached to a heterocyclic group (JY); wherein Y is a heterocyclic group comprising the at least one heteroatom J;

J is a Group 15 or 16 heteroatom contained in Y;

x is the valence of M+1; and $Cat^+$ is a cation component;

and wherein one or more positions on at least two heterocyclic groups (JY) is substituted with a halogen atom or a halogen atom containing group.

2. The catalyst system of claim 1 wherein M is boron or aluminum.

3. The catalyst system of claim 1 wherein J is nitrogen, oxygen, or sulfur.

4. The catalyst system of claim 1 wherein each J is nitrogen, each (JY) is independently a pyrrolyl, imidazolyl, pyrazolyl, pyrrolidinyl, purinyl, carbazolyl, or indolyl group, and each J is attached to M.

5. The catalyst system of claim 1 wherein each (JY) is independently unsubstituted or substituted with one or more substituent(s) selected from hydrogen, halogen, linear or branched alkyl, alkenyl or alkynyl radicals, cycloalkyl radicals, aryl radicals, aryl substituted alkyl radicals, acyl radicals, aroyl radicals, alkoxy radicals, aryloxy radicals, alkylthio radicals, dialkylamino radicals, alkoxycarbonyl radicals, aryloxycarbonyl radicals, carbomoyl radicals, alkyl- or dialkyl-carbamoyl radicals, acyloxy radicals, acylamino radicals, aroylamino radicals, straight, branched or cyclic, or alkylene radicals.

6. The catalyst system of claim 5 wherein one or more of the substituents is halogenated.

7. The catalyst system of claim 1 wherein each (JY) is substituted with a halogen or a halogen containing group.

8. The catalyst system of claim 1 wherein each (JY) is independently represented by the formula:

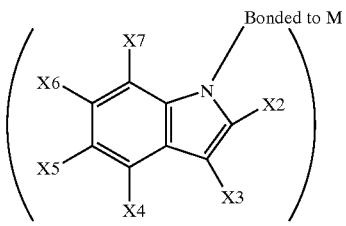

wherein each of X2 to X7 is independently selected from hydrogen, halogen, an alkyl group, a halogenated or partially halogenated alkyl group, an aryl group, a halogenated or partially halogenated aryl group, an aryl substituted alkyl group or a halogenated or partially halogenated aryl substituted alkyl group.

9. The catalyst system of claim 8 wherein each of X4 to X7 is a fluorine atom.

10. The catalyst system of claim 9 wherein X3 is hydrogen, a halogenated or partially halogenated aryl group, an aryl substituted alkyl group, or a halogenated or partially halogenated aryl substituted alkyl group.

11. A catalyst system comprising a catalyst compound and an activator compound wherein the activator compound is represented by the formula:

$$M(JY)_x$$

wherein M is a Group 13 atom attached to a heterocyclic group (JY); wherein Y is a heterocyclic group comprising the at least one heteroatom J;

J is a Group 15 or 16 heteroatom contained in Y; and x is the valence of M; and wherein one or more positions on at least two heterocyclic groups (JY) is substituted with a halogen atom or a halogen atom containing group.

12. The catalyst system of claim 11 wherein M is boron or aluminum.

13. The catalyst system of claim 11 wherein J is nitrogen, oxygen, or sulfur.

14. The catalyst system of claim 11 wherein each J is nitrogen, each (JK) is independently a pyrrolyl, imidazolyl, pyrazolyl, pyrrolidinyl, purinyl, carbazolyl, or indolyl group, and each J is attached to M.

15. The catalyst system of claim 11 wherein each (JY) is independently unsubstituted or substituted with one or more substituent(s) selected from halogen, linear or branched alkyl, alkenyl or alkynyl radicals, cycloalkyl radicals, aryl radicals, aryloxy radicals, alkylthio radicals, dialkylamino radicals, alkoxycarbonyl radicals, aryloxycarbonyl radicals, carbomoyl radicals, alkyl- or dialkyl- carbamoyl radicals, acyloxy radicals, acylamino radicals, aroylamino radicals, straight, branched or cyclic, or alkylene radicals.

16. The catalyst system of claim 15 wherein one or more of the substituents is halogenated.

17. The catalyst system of claim 11 wherein each (JY) is substituted with a halogen or a halogen containing group.

18. The catalyst system of claim 11 wherein each (JY) is independently represented by the formula:

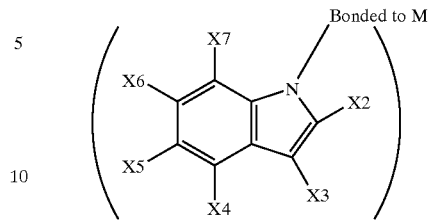

wherein each of X2 to X7 is independently selected from hydrogen, halogen, an alkyl group, a halogenated or partially halogenated alkyl group, an aryl group, a halogenated or partially halogenated aryl group, an aryl substituted alkyl group or a halogenated or partially halogenated aryl substituted alkyl group.

19. The catalyst system of claim 18 wherein each of X4 to X7 is a fluorine atom.

20. The catalyst system of claim 19 wherein X3 is hydrogen, a halogenated or partially halogenated aryl group, an aryl substituted alkyl group, or a halogenated or partially halogenated aryl substituted alkyl group.

21. A process for polymerizing olefin(s) comprising contacting a monomer and optionally a comonomer under polymerization conditions with a catalyst system comprising an activator compound represented by the formula:

$$Cat^+[M(JY)_x]^-$$

wherein M is a Group 13 atom attached to a heterocyclic group (JY); wherein Y is a heterocyclic group comprising the at least one heteroatom J;

J is a Group 15 or 16 heteroatom contained in Y;

x is the valence of M+1; and

Cat$^+$ is a cation component;

and wherein one or more positions on at least two heterocyclic groups (JY) is substituted with a halogen atom or a halogen atom containing group.

22. A process for polymerizing olefin(s) comprising contacting a monomer and optionally a comonomer under polymerization conditions with a catalyst system comprising an activator compound represented by the formula:

$$M(JY)_x$$

wherein M is a Group 13 atom attached to a heterocyclic group (JY), wherein Y is a heterocyclic group comprising the at least one heteroatom J;

J is a Group 15 or 16 heteroatom contained in Y; and x is the valence of M; and wherein one or more positions on at least two heterocyclic groups (JY) is substituted with a halogen atom or a halogen atom containing group.

* * * * *